US007601688B2

(12) United States Patent
Still et al.

(10) Patent No.: US 7,601,688 B2
(45) Date of Patent: *Oct. 13, 2009

(54) METHODS OF REDUCING HYPOGLYCEMIC EPISODES IN THE TREATMENT OF DIABETES MELLITUS

(75) Inventors: James Gordon Still, Raleigh, NC (US); Gordana Kosutic, Raleigh, NC (US)

(73) Assignee: Biocon Limited (IN)

( * ) Notice: Subject to any disclaimer, the term of this patent is extended or adjusted under 35 U.S.C. 154(b) by 462 days.

This patent is subject to a terminal disclaimer.

(21) Appl. No.: 10/461,199

(22) Filed: Jun. 13, 2003

(65) Prior Publication Data
US 2004/0038867 A1 Feb. 26, 2004

Related U.S. Application Data

(63) Continuation-in-part of application No. 10/075,097, filed on Feb. 13, 2002, now Pat. No. 7,060,675.

(60) Provisional application No. 60/269,198, filed on Feb. 15, 2001, provisional application No. 60/347,713, filed on Jan. 11, 2002.

(51) Int. Cl.
*A61K 38/28* (2006.01)
*A61K 47/48* (2006.01)

(52) U.S. Cl. ........................................................ 514/3

(58) Field of Classification Search .................. None
See application file for complete search history.

(56) References Cited

U.S. PATENT DOCUMENTS

| 3,256,153 | A | 6/1966 | Heimlech |
| 3,868,356 | A | 2/1975 | Smyth |
| 3,919,411 | A | 11/1975 | Glass et al. |
| 3,950,517 | A | 4/1976 | Lindsay et al. |
| 4,003,792 | A | 1/1977 | Mill et al. |
| 4,044,196 | A | 8/1977 | Huper et al. |
| 4,087,390 | A | 5/1978 | Shields |
| 4,093,574 | A | 6/1978 | Shields |
| 4,100,117 | A | 7/1978 | Shields |
| 4,179,337 | A | 12/1979 | Davis et al. |
| 4,223,163 | A | 9/1980 | Guilloty |
| 4,229,438 | A | 10/1980 | Fujino et al. |
| 4,253,998 | A | 3/1981 | Sarantakis |
| 4,277,394 | A | 7/1981 | Fujino et al. |
| 4,338,306 | A | 7/1982 | Kitao et al. |
| 4,348,387 | A | 9/1982 | Brownlee et al. |
| 4,410,547 | A | 10/1983 | Ueno et al. |
| 4,469,681 | A | 9/1984 | Brownlee et al. |
| 4,472,382 | A | 9/1984 | Labrie et al. |
| 4,554,101 | A | 11/1985 | Hopp |
| 4,579,730 | A | 4/1986 | Kidron et al. |
| 4,585,754 | A | 4/1986 | Meisner et al. |
| 4,602,043 | A | 7/1986 | Geho |
| 4,622,392 | A | 11/1986 | Hong et al. |
| 4,662,872 | A | 5/1987 | Cane |
| 4,684,524 | A | 8/1987 | Eckenhoff et al. |
| 4,698,264 | A | 10/1987 | Steinke |
| 4,704,394 | A | 11/1987 | Geho |
| 4,717,566 | A | 1/1988 | Eckenhoff et al. |
| 4,744,976 | A | 5/1988 | Snipes et al. |
| 4,761,287 | A | 8/1988 | Geho |
| 4,772,471 | A | 9/1988 | Vanlerberghe et al. |
| 4,797,288 | A | 1/1989 | Sharma et al. |
| 4,801,575 | A | 1/1989 | Pardridge |
| 4,822,337 | A | 4/1989 | Newhouse et al. |
| 4,839,341 | A | 6/1989 | Massey et al. |
| 4,840,799 | A | 6/1989 | Appelgren et al. |
| 4,849,405 | A | 7/1989 | Ecanow |
| 4,863,896 | A | 9/1989 | Geho et al. |
| 4,917,888 | A | 4/1990 | Katre et al. |
| 4,935,246 | A | 6/1990 | Ahrens |
| 4,946,828 | A | 8/1990 | Markussen |
| 4,957,910 | A | 9/1990 | Sutton et al. |
| 4,963,367 | A | 10/1990 | Ecanow |
| 4,963,526 | A | 10/1990 | Ecanow |
| 4,994,439 | A | 2/1991 | Longenecker et al. |
| 5,013,556 | A | 5/1991 | Woodle et al. |
| 5,055,300 | A | 10/1991 | Gupta |
| 5,055,304 | A | 10/1991 | Makino et al. |
| 5,089,261 | A | 2/1992 | Nitecki et al. |
| 5,093,198 | A | 3/1992 | Speaker et al. |
| 5,099,074 | A | 3/1992 | Mueller et al. |
| 5,122,614 | A | 6/1992 | Zalipsky |

(Continued)

FOREIGN PATENT DOCUMENTS

DE 19632440 A1 2/1998

(Continued)

OTHER PUBLICATIONS

S. Clement, et al. Diabetes (2000) 51(suppl 2) Abstract 11-LB.*

(Continued)

*Primary Examiner*—Andrew D Kosar
(74) *Attorney, Agent, or Firm*—Marianne Fuierer; Moore & Van Allen PLLC

(57) ABSTRACT

The present invention provides compositions and methods for reducing hypoglycemic episodes experienced by a subject in need of treatment for diabetes mellitus, said method comprising orally administering an amount of an insulin polypeptide-oligomer conjugate to the subject, wherein: i) the amount of the insulin polypeptide-oligomer conjugate reduces the number and/or severity of hypoglycemic episodes experienced by the subject during a given time period when compared with the number and/or severity of hypoglycemic episodes that would have been experienced during a similar time period by the subject or by subjects in a control group parenterally administered insulin or an insulin analog in an amount that provides a substantially equivalent level of glycemic control; and ii) the oligomer of the insulin polypeptide-oligomer conjugate comprises a hydrophilic moiety and a lipophilic moiety.

10 Claims, 2 Drawing Sheets

U.S. PATENT DOCUMENTS

| | | |
|---|---|---|
| 5,157,021 A | 10/1992 | Balschmidt et al. |
| 5,162,430 A | 11/1992 | Rhee et al. |
| 5,164,366 A | 11/1992 | Balschmidt et al. |
| 5,202,415 A | 4/1993 | Jonassen et al. |
| 5,206,219 A | 4/1993 | Desai |
| 5,283,236 A | 2/1994 | Chiou |
| 5,286,637 A | 2/1994 | Veronese et al. |
| 5,292,802 A | 3/1994 | Rhee et al. |
| 5,298,410 A | 3/1994 | Phillips et al. |
| 5,304,473 A | 4/1994 | Belagaje et al. |
| 5,308,889 A | 5/1994 | Rhee et al. |
| 5,312,808 A | 5/1994 | Shorr et al. |
| 5,320,094 A | 6/1994 | Laube et al. |
| 5,320,840 A | 6/1994 | Camble et al. |
| 5,321,009 A | 6/1994 | Baeder et al. |
| 5,324,775 A | 6/1994 | Rhee et al. |
| 5,328,955 A | 7/1994 | Rhee et al. |
| 5,349,052 A | 9/1994 | Delgado et al. |
| 5,359,030 A | 10/1994 | Ekwuribe |
| 5,364,838 A | 11/1994 | Rubsamen |
| 5,405,621 A | 4/1995 | Sipos |
| 5,405,877 A | 4/1995 | Greenwald et al. |
| 5,413,791 A | 5/1995 | Rhee et al. |
| 5,415,872 A | 5/1995 | Sipos |
| 5,420,108 A | 5/1995 | Shohet |
| 5,428,128 A | 6/1995 | Mensi-Fattohi et al. |
| 5,438,040 A | 8/1995 | Ekwuribe |
| 5,444,041 A | 8/1995 | Owen et al. |
| 5,446,091 A | 8/1995 | Rhee et al. |
| 5,457,066 A | 10/1995 | Frank et al. |
| 5,461,031 A | 10/1995 | De Felippis |
| 5,468,478 A | 11/1995 | Saifer et al. |
| 5,468,727 A | 11/1995 | Phillips et al. |
| 5,504,188 A | 4/1996 | Baker et al. |
| 5,506,203 A | 4/1996 | Backstrom et al. |
| 5,518,998 A | 5/1996 | Backstrom et al. |
| 5,523,348 A | 6/1996 | Rhee et al. |
| 5,529,915 A | 6/1996 | Phillips et al. |
| 5,545,618 A | 8/1996 | Buckley et al. |
| 5,550,188 A | 8/1996 | Rhee et al. |
| 5,567,422 A | 10/1996 | Greenwald |
| 5,597,797 A | 1/1997 | Clark et al. |
| 5,606,038 A | 2/1997 | Regen |
| 5,612,460 A | 3/1997 | Zalipsky |
| 5,631,347 A | 5/1997 | Baker et al. |
| 5,637,749 A | 6/1997 | Greenwald |
| 5,643,575 A | 7/1997 | Martinez et al. |
| 5,646,242 A | 7/1997 | Baker et al. |
| 5,650,388 A | 7/1997 | Shorr et al. |
| 5,658,878 A | 8/1997 | Backstrom et al. |
| 5,681,277 A | 10/1997 | Baker et al. |
| 5,681,811 A | 10/1997 | Ekwuribe |
| 5,693,609 A | 12/1997 | Baker et al. |
| 5,693,769 A | 12/1997 | Kahne et al. |
| 5,700,904 A | 12/1997 | Baker et al. |
| 5,704,910 A | 1/1998 | Humes |
| 5,707,648 A | 1/1998 | Yiv |
| 5,714,519 A | 2/1998 | Cincotta et al. |
| 5,714,639 A | 2/1998 | Bowman et al. |
| 5,738,846 A | 4/1998 | Greenwald et al. |
| 5,747,445 A | 5/1998 | Backstrom et al. |
| 5,747,642 A | 5/1998 | De Felippis |
| 5,750,497 A | 5/1998 | Havelund et al. |
| 5,763,396 A | 6/1998 | Weiner et al. |
| 5,766,620 A | 6/1998 | Heiber et al. |
| 5,824,638 A | 10/1998 | Burnside et al. |
| 5,830,853 A | 11/1998 | Backstrom et al. |
| 5,830,918 A | 11/1998 | Sportsman et al. |
| 5,843,886 A | 12/1998 | Weiner et al. |
| 5,849,860 A | 12/1998 | Hakimi et al. |
| 5,853,748 A | 12/1998 | New |
| 5,854,208 A | 12/1998 | Jones et al. |
| 5,856,451 A | 1/1999 | Olsen et al. |
| 5,866,538 A | 2/1999 | Norup et al. |
| 5,866,584 A | 2/1999 | Cincotta et al. |
| 5,874,111 A | 2/1999 | Maitra et al. |
| 5,889,153 A | 3/1999 | Suzuki et al. |
| 5,898,028 A | 4/1999 | Jensen et al. |
| 5,902,588 A | 5/1999 | Greenwald et al. |
| 5,905,140 A | 5/1999 | Hansen |
| 5,907,030 A | 5/1999 | Shen et al. |
| 5,922,675 A | 7/1999 | Baker et al. |
| 5,932,462 A | 8/1999 | Harris et al. |
| 5,942,248 A | 8/1999 | Barnwell |
| 5,948,751 A | 9/1999 | Kimer et al. |
| 5,952,008 A | 9/1999 | Backstrom et al. |
| 5,952,297 A | 9/1999 | De Felippis et al. |
| 5,962,267 A | 10/1999 | Shin et al. |
| 5,968,549 A | 10/1999 | New et al. |
| 5,969,040 A | 10/1999 | Hallahan et al. |
| 5,981,709 A | 11/1999 | Greenwald et al. |
| 5,985,263 A | 11/1999 | Lee et al. |
| 5,997,848 A | 12/1999 | Patton et al. |
| 6,004,574 A | 12/1999 | Backstrom et al. |
| 6,011,008 A | 1/2000 | Domb et al. |
| 6,025,325 A | 2/2000 | Campfield et al. |
| 6,034,054 A | 3/2000 | De Felippis et al. |
| 6,042,822 A | 3/2000 | Gilbert et al. |
| 6,043,214 A | 3/2000 | Jensen et al. |
| 6,051,551 A | 4/2000 | Hughes et al. |
| 6,057,292 A | 5/2000 | Cunningham et al. |
| 6,063,761 A | 5/2000 | Jones et al. |
| 6,093,391 A | 7/2000 | Kabanov et al. |
| 6,113,906 A | 9/2000 | Greenwald et al. |
| 6,147,108 A | 11/2000 | Hauptman |
| 6,165,976 A | 12/2000 | Backstrom et al. |
| 6,177,087 B1 | 1/2001 | Greenwald et al. |
| 6,191,105 B1 | 2/2001 | Ekwuribe et al. |
| 6,200,602 B1 | 3/2001 | Watts et al. |
| 6,211,144 B1 | 4/2001 | Havelund |
| 6,248,363 B1 | 6/2001 | Patel et al. |
| 6,251,856 B1 | 6/2001 | Markussen et al. |
| 6,258,377 B1 | 7/2001 | New et al. |
| 6,268,335 B1 | 7/2001 | Brader |
| 6,306,440 B1 | 10/2001 | Backstrom et al. |
| 6,309,633 B1 | 10/2001 | Ekwuribe et al. |
| 6,310,038 B1 | 10/2001 | Havelund |
| 6,323,311 B1 | 11/2001 | Liu et al. |
| 6,335,316 B1 | 1/2002 | Hughes et al. |
| 6,342,225 B1 | 1/2002 | Jones et al. |
| 6,506,730 B1 | 1/2003 | Lee et al. |
| 6,858,580 B2 * | 2/2005 | Ekwuribe et al. ............... 514/2 |
| 6,867,183 B2 * | 3/2005 | Soltero et al. .................. 514/3 |
| 7,030,082 B2 | 4/2006 | Soltero |
| 7,196,059 B2 * | 3/2007 | Soltero et al. .................. 514/3 |
| 2002/0160938 A1 | 10/2002 | Brandenberg et al. |
| 2003/0004304 A1 | 1/2003 | Ekwuribe et al. |
| 2003/0027748 A1 | 2/2003 | Ekwuribe et al. |
| 2003/0027995 A1 | 2/2003 | Ekwuribe et al. |
| 2003/0050228 A1 * | 3/2003 | Ekwuribe et al. ............... 514/3 |
| 2003/0060606 A1 | 3/2003 | Ekwuribe et al. |
| 2003/0069170 A1 | 4/2003 | Soltero et al. |
| 2003/0083232 A1 | 5/2003 | Soltero et al. |
| 2003/0087808 A1 | 5/2003 | Soltero et al. |
| 2003/0144468 A1 | 7/2003 | Ekwuribe et al. |
| 2003/0229009 A1 | 12/2003 | Soltero et al. |
| 2004/0038866 A1 | 2/2004 | Soltero et al. |

FOREIGN PATENT DOCUMENTS

| | | |
|---|---|---|
| EP | 0 031 567 | 7/1981 |
| EP | 0511903 | 4/1992 |
| EP | 0 483 465 A1 | 8/1995 |
| EP | 0 483 465 B1 | 8/1995 |

| | | |
|---|---|---|
| EP | 0 621 777 | 9/1996 |
| EP | 0 597 007 | 10/1996 |
| EP | 0797615 B1 | 1/1997 |
| EP | 0 822 218 A2 | 2/1998 |
| GB | 1 492 997 | 11/1977 |
| JP | 01207320 | 8/1989 |
| JP | 1 254 699 | 10/1989 |
| WO | WO93/01802 | 2/1993 |
| WO | WO95/09831 | 4/1995 |
| WO | WO95/30641 | 11/1995 |
| WO | WO97/14740 | 4/1997 |
| WO | WO98/07745 | 2/1998 |
| WO | WO99/32134 | 7/1999 |
| WO | WO99/65941 | 12/1999 |
| WO | WO01/12230 | 2/2001 |

OTHER PUBLICATIONS

B. Radha Krishnan, et al. Proc. Int. Sym. Control. Rel. Bioact. Mater. (1998) 25, 124-125.*

Allaudeen et al. "Orally Active Insulin: A Single Insulin Conjugate Selected for Future Studies" 60th Annual Meeting of the American Diabetes Assoc., Atlanta, GA, Jun. 2000 (Abstract).

Allcock & Lampe "Contemporary Polymer Chemistry" $2^{nd}$ ed., pp. 394-403 (1991).

Anderson et al. "HIM2, a Novel Modified Insulin, has Improved Systemic Pharmacokinetics in Normal Dogs, Compared to Unmodified Insulin" American Diabetes Association 62nd Annual Meeting, Jun. 2002 (Abstract).

Baudys et al. "Synthesis and Characterization of Different Glycosylated Derivatives of Insulin" Proceed. Intern. Symp. Cont. Rel. Bioactive. Mater. 19:210-211 (1992).

Bone et al. "Successful Treatment of an Insulin Dependent Rat Model of Human Type 1 Diabetes with Orally Active Insulin" Program and Abstracts, 4th International Workshop on Lessions from Animal Diabetes, Omiya, Japan, Nov. 1994 (Abstract).

Bone et al. "Successful Treatment of Type 1 Diabetes with Orally-Active Insulin: Studies in The Insulin Dependent BB/S Rat" Program and Abstracts, 55th Annual Meeting of the American Diabetes Association, Atlanta Georgia, Jun. 1995 (Abstract).

Brange and Volund "Insulin Analogs with Improved Pharmacokinetic Profiles" *Advanced Drug Delivery Reviews* 35:307-335 (1999).

Cleland et al. "Emerging Protein Delivery Methods" *Current Opinion in Biotechnology* 12:212-219 (2001).

Clement et al. "Effects of Multiple Doses of Orally Administered Hexyl Insulin M2 (HIM2) on Postprandial Blood Glucose (PPG) Concentrations in Type 1 Diabetic (T1) Patients" American Diabetes Association 62nd Annual Meeting, Jun. 2002 (Poster).

Clement et al. "Oral Insulin Product Hexyl-Insulin Monoconjugate 2 (HIM2) in Type 1 Diabetes Mellitus: The Glucose Stabilization Effects of HIM2" *Diabetes Technology & Therapeutics* 4(4):459-466 (2002).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Abstract).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Poster).

Damge et al. "Poly(alkyl cyanoacrylate) Nanospheres for Oral Administration of Insulin" *Journal of Pharmaceutical Sciences* 86(12):1403-1409 (Dec. 1997).

Dandona et al. "Effects of an Oral Modified Insulin on Blood Glucose Levels in Fasting and Fed Type 1 Diabetic Patients Receiving a 'Basal' Regimen of Injected Insulin" American Diabetes Association Annual Meeting (Jun. 25, 2001) (Abstract).

Ekwuribe et al. "Oral Insulin Delivery: Hydrolyzable Amphiphilic Oligomer Conjugates Prolong Glucose Reduction" *Proceed. Int'l. Symp. Control. Rel. Biooact. Mater.* 26:147-148 (1999).

Ekwuribe et al. *Calcitonin Drug-Oligomer Conjugates, and Uses Thereof*, U.S. Appl. No. 10/166,355, filed Nov. 08, 2002, including Preliminary Amendement dated Feb. 26, 2003 and Supplemental Preliminary Amendment dated Mar. 31, 2003.

Ekwuribe et al. *Mixtures of Drug-Oligomer Conjugates Comprising Polyalkylene Glycol, Uses Thereof, and Methods of Making Same*, U.S. Appl. No. 09/873,797, filed Jun. 4, 2001.

Ekwuribe, Nnochiri "Conjugation-Stabilized Polypeptide Compositions, Therapeutic Delivery and Diagnostic Formulations Comprising Same, and Method of Making and Using the Same" *Biotechnology Advances* 14(4):575-576 (1996) (Abstract).

Forst et al. "New Aspects on Biological Activity of C-peptide in IDDM Patients" *Exp. Clin. Endocrinol. Diabetes* 106:270-276 (1998).

Francis et al. Polyethylene Glycol Modification: Relevance of Improved Methodology to Tumour Targeting, Journal of Drug Targeting 3:321-340 (1996).

Guzman et al. "Effects of Fatty Ethers and Stearic Acid on the Gastrointestinal Absorption of Insulin" *PRHSJ* 9(2):155-159 (1990).

Hinds et al. "Synthesis and Characterization of Poly(ethylene glycol)-Insulin Conjugates" *Bioconjugate Chem*. 11:195-201 (2000).

Igarashi et al. "Biologically Active Peptides Conjugated with Lecithin for DDS" *Proceed. Intern. Symp. Cont. Rel. Bioactiv. Mater.* 17:367-368 (1990).

Kipnes et al. "The Effects of an Oral Modified Insuling on Postprandial Blood Glucose Levels in Patients with Type 2 Diabetes" American Diabetes Association Annual Meeting (Jun. 24, 2001) (Abstract).

Kube, D.M. "Multitalented Proteins Play a Key Role in Therapeutics" *Genomics and Proteomics* (Sep. 2002).

Lindsay et al. *The Acetylation of Insulin Biochem J.* 121:737-745 (1971).

Marschutz et al. "Oral Peptide Drug Delivery: Polymer-Inhibitor Conjugates Protecting Insulin from Enzymatic Degradation In Vitro" *Biomaterials* 21:1499-1507 (2000).

Pauletti et al. "Improvement of Oral Peptide Bioavailability: Peptidomimetics and Prodrug Strategies" *Advanced Drug Delivery Reviews* 27:235-256 (1997.

Radhakrishnan et al. "Oral Delivery of Insulin: Single Selective Modification at B29-LYS With Amphiphilic Oligomer" Program and Abstracts, 1999 National Meeting of the Ameri. Assoc. Pharm. Scient., New Orleans, LA (1999) (Abstract).

Radakrishnan et al. "Stability and Physical Characteristics of Orally Active Amphiphilic Human Insulin Analog, Methoxy (Polyethylene Glycol) Hexanoyl Human Recombinant Insulin (HIM2)" *Proceed. Int'l. Symp. Control. Rel. Bioact. Mater.* 27:1038-39 (2000).

Radhakrishnan et al.. *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.

Still and McAllister "Effects of Orally Active Modified Insulin in Type 1 Diabetic Patients" *Clinical Pharmacol. Therap.* 69(2):P95 (Feb. 2001) (Abstract).

Aoki et al. "Chronic Intermittent Intravenous Insulin Therapy: A New Frontier in Diabetes Therapy" *Diabetes Technology & Therapeutics* 3(1):111-123 (2001).

Inernational Search Report for International Application No. PCT/US03/18763 dated Jan. 12, 2004.

Liu et al. "Glucose-Induced Release of Glycosylpoly(ethylene glycol) Insulin Bound to a Soluble Conjugate of Concanavalin A" *Bioconjugate Chem*. 8:664-672 (1997).

Michael et al. "Loss of Insulin Signaling in Hepatocytes Leads to Severe Insulin Resistance and Progressive Hepatic Dysfunction" *Molecular Cell* 6:87-97 (1999).

Sindelar et al. "A Comparison of the Effects of Selective Increases in Peripheral or Portal Insulin on Hepatic Glucose Production in the Conscious Dog" *Diabetes* 45:1594-1604 (1996).

* cited by examiner

METHODS OF REDUCING HYPOGLYCEMIC EPISODES IN THE TREATMENT OF DIABETES MELLITUS

CROSS REFERENCE TO RELATED APPLICATIONS

This application is a Continuation-in-Part of U.S. application Ser. No. 10/075,097 filed on Feb. 13, 2003, titled "METHOD OF TREATING DIABETES MELLITUS" now U.S. Pat. No. 7,060,675, which in turn claims priority to U.S. Provisional Application No. 60/347,713, filed on Jan. 11, 2002 and U.S. Provisional Application No. 60/269,198, filed on Feb. 15, 2001.

FIELD OF THE INVENTION

The present invention relates to methods of treating diabetes mellitus.

BACKGROUND OF THE INVENTION

There are currently 15.7 million people or 5.9% of the population in the United States who suffer from diabetes mellitus. Each day approximately 2,200 people are diagnosed with diabetes and roughly 798,000 people will be diagnosed this year. Diabetes is the seventh leading cause of death (sixth-leading cause of death by disease) in the United States.

Diabetes mellitus, more commonly known as diabetes, is a disease in which the body does not produce and/or properly use insulin, a hormone that aids the body in converting sugars and other foods into energy. In a non-diabetic individual, insulin is produced in the pancreas at the islets of Langerhans in response to an increase of glucose in the gut and/or blood. Insulin then acts in conjunction with the liver to control glucose metabolism in the body. While diabetes is typically thought of as a blood-sugar disease, diabetes may result in numerous life-threatening complications. For example, diabetes may lead to various microvascular diseases, such as retinopathy, nephropathy, and neuropathy. In the United States, diabetes is the leading cause of new cases of blindness in people ages 20 to 74, is the leading cause of end-stage renal disease, and is the most frequent cause of lower limb amputations. Diabetic individuals also have a higher likelihood of developing life-threatening macrovascular diseases, such as heart disease and stroke.

Several types of diabetes exist. Insulin dependent diabetes mellitus (IDDM), commonly referred to as Type 1 diabetes, is an auto-immune disease that affects the islets of Langerhans, destroying the body's ability to produce insulin. Type 1 diabetes may affect as many as 1 million people in the United States. Non-insulin dependent diabetes mellitus (NIDDM), commonly referred to as Type 2 diabetes, is a metabolic disorder resulting from the body's inability to produce enough insulin or properly use the insulin produced. Roughly 90 percent of all diabetic individuals in the United States suffer from Type 2 diabetes, which is usually associated with obesity and a sedentary lifestyle.

In general, the goal of diabetes treatment is to control glucose level in the blood and maintain it in a range that mimics that of a non-diabetic individual, namely reproduces natural physiological glucose homeostasis. A recent study called the Diabetes Control and Complications Trial (DCCT) found that keeping blood sugar levels as close to normal as possible significantly reduced the damage to eyes, kidneys, and nerves caused by high blood sugar. The DCCT studied 1,400 Type 1 diabetics for an average of seven years to find out if significantly lowering blood glucose levels would reduce diabetic complications such as eye, nerve, or kidney disease. Half the study group continued their usual treatment plan, while the other half maintained extremely tight control over their blood sugar levels—attempting to keep those levels as close to those of nondiabetic people at all times.

Overall, people who exercised tight control over their blood sugar had significantly less damage to their eyes, kidneys, and nerves. For example, diabetic eye disease started in only one-quarter as many people, kidney disease started in only half as many people, nerve disease started in only one-third as many people, and far fewer people who already had early forms of these three complications got worse. In fact, the results were so striking that doctors ended the trial early in order to bring all patients over to the tight control treatment. Because of the significant decrease in diabetic complications, the American Diabetes Association recommends maintaining tight control over blood sugar levels in all Type 1 diabetics. However, tight control treatment utilizing conventional injectable insulin therapies may present risks that outweigh these benefits for some patients.

The DCCT reported that people in the tight control group had triple the normal risk of low blood sugar (hypoglycemic) episodes. The brain relies exclusively on glucose for energy, so extremely low blood sugar levels can result in tiredness, headache, confusion, or even unconsciousness. This increased risk of hypoglycemic episodes may have prompted the American Diabetes Association to recommend that certain individuals refrain from attempting to maintain a tight control regimen, despite the long-term benefits that tight control treatment may provide. For example, children should not be put on a program of tight control because having enough glucose in the blood is vital to brain development. As another example, elderly people probably should not go on tight control. Hypoglycemia can cause strokes and heart attacks in older people. As yet another example, some people who already have complications associated with diabetes mellitus should not be on tight control. As still other examples, people with end-stage kidney disease or severe vision loss probably should not attempt to achieve tight control. Some people who have coronary artery disease or vascular disease probably should not try tight control. As yet another example, people who often have low blood glucose reactions probably should not go on tight control. Thus, the increased risk of hypoglycemia when utilizing a conventional injection therapy regimen to maintain tight control of blood glucose may prevent many people, who would otherwise benefit from such a regimen, from pursuing this course of treatment.

The increased risk of hypoglycemia may make maintaining tight regulation using conventional injectable insulin therapies a time consuming endeavor. To achieve tight control utilizing conventional injectable insulin therapies, individuals suffering from diabetes must pay more attention to their diet and exercise. They must measure their blood glucose levels more often. They must provide themselves with a low level of insulin at all times and take extra insulin when they eat. The American Diabetes Association recommends two conventional ways of providing a more natural level of insulin: multiple daily injection therapy and an insulin pump. In multiple daily injection therapy, the diabetic patient takes three or more insulin shots per day—usually a shot of short-acting or regular insulin before each meal and a shot of intermediate- or long-acting insulin at bedtime. With an insulin pump, the diabetic patient wears a tiny pump that releases insulin into his or her body through a plastic tube. The pump usually gives a constant small dose of short-acting or Regular insulin, and may be manipulated to release extra insulin when needed, such as before a meal. With either method, the diabetic patient should test his or her blood glucose levels several times a day, for example before each shot or extra dose of insulin to know how many units to take and how long before eating to take them, two or three hours after eating to make sure he or she took enough insulin, and before driving.

The increased risk of hypoglycemia may make pursuing a tight regulation regimen that utilizes conventional injection therapies a costly course of treatment. Ensuring an acceptable risk of hypoglycemia may involve employing a health care team that includes a doctor, a dietitian, a diabetes educator, a mental health professional, and other health care professionals, who may need to spend a lot of time with the patient to determine the precise timing and doses of insulin needed and the lifestyle changes needed to maintain tight control using conventional insulin injection therapies without undue risk of hypoglycemia. The diabetic patient may even need to stay in the hospital for a few days so that the health care team can monitor blood glucose and be close at hand in the event any hypoglycemic episodes are experienced by the patient as the tight control regimen is determined. Even after determining the regimen, the monitoring costs of maintaining the regimen may be quite high.

In view of the foregoing, there is a need in the art for methods of treating diabetes mellitus that provide a reduced risk of hypoglycemic episodes.

SUMMARY OF THE INVENTION

Embodiments of methods of the present invention reduce the hypoglycemic episodes experienced by a subject in need of treatment for diabetes mellitus. By reducing the hypoglycemic episodes experienced by the subject, methods according to embodiments of the present invention may reduce the risk associated with achieving tight control of the subject's blood glucose levels, allowing the subject in need of treatment for diabetes mellitus to pursue a tight control treatment regimen. This reduced risk of hypoglycemia may allow patients who are currently discouraged from pursuing a tight control regimen, such as children and juveniles, the elderly, patients who have a tendency to experience low blood glucose reactions, patients suffering from coronary heart disease, patients suffering from end-stage kidney disease, and patients having severe vision loss as a complication resulting from diabetes mellitus, to pursue a tight control regimen. Accordingly, methods according to embodiments of the present invention may aid these patients in living longer and more enjoyable lives.

According to embodiments of the present invention, a method for reducing hypoglycemic episodes experienced by a subject in need of treatment for diabetes mellitus includes orally administering an effective amount of an insulin drug of this invention to the subject thereby reducing the number and/or severity of hypoglycemic episodes experienced by the subject during a given time period when compared with the number and/or severity of hypoglycemic episodes that would have been experienced by the subject during a similar time period to obtain an equivalent or a substantially equivalent level of glycemic control utilizing parenteral administration of insulin or an insulin analog.

Also provided herein is a method for reducing hypoglycemic episodes experienced by a subject in need of treatment for diabetes mellitus, said method comprising orally administering an amount of an insulin polypeptide-oligomer conjugate to the subject, wherein: i) the amount of the insulin polypeptide-oligomer conjugate reduces the number and/or severity of hypoglycemic episodes experienced by the subject during a given time period when compared with the number and/or severity of hypoglycemic episodes that would have been experienced during a similar time period by subjects in a control group parenterally administered insulin or an insulin analog in an amount that provides an equivalent or a substantially equivalent level of glycemic control; and ii) the oligomer of the insulin polypeptide-oligomer conjugate comprises a hydrophilic moiety and a lipophilic moiety.

According to other embodiments of the present invention, a method for providing tight control of blood glucose in a subject in need of treatment for diabetes mellitus includes orally administering an effective amount of an insulin drug of this invention to the subject to provide tight control of blood glucose in the subject.

According to still other embodiments of the present invention, a method for controlling blood glucose between about 70 and 120 mg/dl before meals and less than about 180 mg/dl after meals in a subject in need of treatment for diabetes mellitus includes orally administering an effective amount of an insulin drug of this invention to the subject to control blood glucose in the subject between about 70 and 120 mg/dl before meals and less than about 180 mg/dl after meals.

According to yet other embodiments of the present invention, a method for maintaining a glycated hemogloblin level of less than about 7 percent in a subject in need of treatment for diabetes mellitus includes orally administering an effective amount of an insulin drug of this invention to the subject to maintain a glycated hemoglobin level in the subject of less than about 7 percent.

According to other embodiments of the present invention, a method for reducing low blood glucose reactions in a subject having a tendency to experience low blood glucose reactions following parenteral administration of insulin or an insulin analog includes orally administering an effective amount of an insulin drug of this invention to the subject thereby reducing the number of low blood glucose reactions experienced by the subject.

According to still other embodiments of the present invention, a method for providing tight control of blood glucose in a subject in need of treatment for diabetes mellitus and having a tendency to experience low blood glucose reactions following parenteral administration of insulin or an insulin analog includes orally administering an effective amount of an insulin drug of this invention to the subject to provide tight control of blood glucose in the subject.

According to yet other embodiments of the present invention, a method for controlling blood glucose between about 70 and 120 mg/dl before meals and less than about 180 mg/dl after meals in a subject in need of treatment for diabetes mellitus and having a tendency to experience low blood glucose reactions following parenteral administration of insulin or an insulin analog includes orally administering an effective amount of an insulin drug of this invention to the subject to control blood glucose in the subject between about 70 and 120 mg/dl before meals and less than about 180 mg/dl after meals.

According to other embodiments of the present invention, a method for maintaining a glycated hemogloblin level of less than about 7 percent in a subject in need of treatment for diabetes mellitus and having a tendency to experience low blood glucose reactions following parenteral administration of insulin or an insulin analog includes orally administering an effective amount of an insulin drug of this invention to the subject to maintain a glycated hemoglobin level in the subject of less than about 7 percent.

According to still other embodiments of the present invention, a method for providing tight control of blood glucose in a patient who is 12 years of age or younger and is in need of treatment for diabetes mellitus includes orally administering an effective amount of an insulin drug of this invention to the patient to provide tight control of blood glucose in the patient.

According to yet other embodiments of the present invention, a method for controlling blood glucose between about 70 and 120 mg/dl before meals and less than about 180 mg/dl after meals in a patient who is 12 years of age or younger and is in need of treatment for diabetes mellitus includes orally administering an effective amount of an insulin drug of this invention to the patient to control blood glucose in the patient between about 70 and 120 mg/dl before meals and less than about 180 mg/dl after meals.

According to other embodiments of the present invention, a method for maintaining a glycated hemogloblin level of less than about 7 percent in a patient who is 12 years of age or younger and is in need of treatment for diabetes mellitus includes orally administering an effective amount of an insulin drug of this invention to the patient to maintain a glycated hemoglobin level in the patient of less than about 7 percent.

According to other embodiments of the present invention, a method for providing tight control of blood glucose in a patient who is 65 years of age or older and is in need of treatment for diabetes mellitus includes orally administering an effective amount of an insulin drug of this invention to the patient to provide tight control of blood glucose in the patient.

According to still other embodiments of the present invention, a method for controlling blood glucose between about 70 and 120 mg/dl before meals and less than about 180 mg/dl after meals in a patient who is 65 years of age or older and is in need of treatment for diabetes mellitus includes orally administering an effective amount of an insulin drug of this invention to the patient to control blood glucose in the patient between about 70 and 120 mg/dl before meals and less than about 180 mg/dl after meals.

According to yet other embodiments of the present invention, a method for maintaining a glycated hemogloblin level of less than about 7 percent in a patient who is 65 years of age or older and is in need of treatment for diabetes mellitus includes orally administering an effective amount of an insulin drug of this invention to the patient to maintain a glycated hemoglobin level in the patient of less than about 7 percent.

According to other embodiments of the present invention, a method for providing tight control of blood glucose in a patient who has coronary heart disease and is in need of treatment for diabetes mellitus includes orally administering an effective amount of an insulin drug of this invention to the patient to provide tight control of blood glucose in the patient.

According to still other embodiments of the present invention, a method for controlling blood glucose between about 70 and 120 mg/dl before meals and less than about 180 mg/dl after meals in a patient who has coronary heart disease and is in need of treatment for diabetes mellitus includes orally administering an effective amount of an insulin drug of this invention to the patient to control blood glucose in the patient between about 70 and 120 mg/dl before meals and less than about 180 mg/dl after meals.

According to yet other embodiments of the present invention, a method for maintaining a glycated hemogloblin level of less than about 7 percent in a patient who has coronary heart disease and is in need of treatment for diabetes mellitus includes orally administering an effective amount of an insulin drug of this invention to the patient to maintain a glycated hemoglobin level in the patient of less than about 7 percent.

According to still other embodiments of the present invention, a method for providing tight control of blood glucose in a patient who has end-stage kidney disease and is in need of treatment for diabetes mellitus includes orally administering an effective amount of an insulin drug of this invention to the patient to provide tight control of blood glucose in the patient.

According to other embodiments of the present invention, a method for controlling blood glucose between about 70 and 120 mg/dl before meals and less than about 180 mg/dl after meals in a patient who has end-stage kidney disease and is in need of treatment for diabetes mellitus includes orally administering an effective amount of an insulin drug of this invention to the patient to control blood glucose in the patient between about 70 and 120 mg/dl before meals and less than about 180 mg/dl after meals.

According to still other embodiments of the present invention, a method for maintaining a glycated hemogloblin level of less than about 7 percent in a patient who has end-stage kidney disease and is in need of treatment for diabetes mellitus includes orally administering an effective amount of an insulin drug of this invention to the patient to maintain a glycated hemoglobin level in the patient of less than about 7 percent.

According to yet other embodiments of the present invention, a method for providing tight control of blood glucose in a patient who has severe vision loss as a complication resulting from diabetes mellitus includes orally administering an effective amount of an insulin drug of this invention to the patient to provide tight control of blood glucose in the patient.

According to other embodiments of the present invention, a method for controlling blood glucose between about 70 and 120 mg/dl before meals and less than about 180 mg/dl after meals in a patient who has severe vision loss as a complication resulting from diabetes mellitus includes orally administering an effective amount of an insulin drug of this invention to the subject to control blood glucose in the subject between about 70 and 120 mg/dl before meals and less than about 180 mg/dl after meals.

According to still other embodiments of the present invention, a method for maintaining a glycated hemogloblin level of less than about 7 percent in a patient who has severe vision loss as a complication resulting from diabetes mellitus includes orally administering an effective amount of an insulin drug of this invention to the patient to maintain a glycated hemoglobin level in the patient of less than about 7 percent.

DETAILED DESCRIPTION OF PREFERRED EMBODIMENTS

Figure 1:
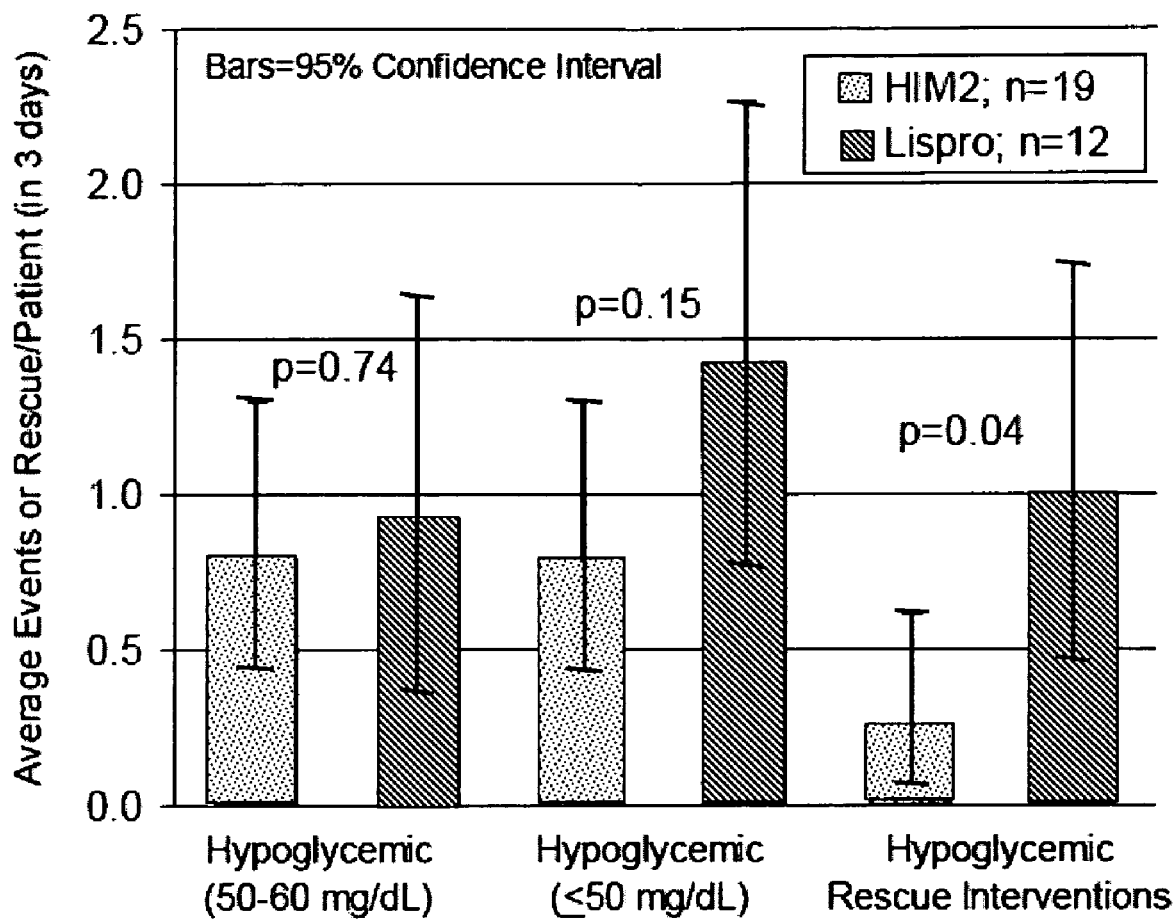
FIG. 1 shows a comparison between hypoglycemic events/rescues experienced by patients using methods according to embodiments of the present invention and hypoglycemic events/rescues experienced by patients using conventional injectable insulin (Lispro) therapy.

The invention will now be described with respect to preferred embodiments described herein. It should be appreciated however that these embodiments are for the purpose of illustrating the invention, and are not to be construed as limiting the scope of the invention as defined by the claims.

As used herein, the term "hypoglycemic episode" refers to a blood glucose level in a subject of less than 60 mg/dL that results in typical symptoms of hypoglycemia such as sweatiness, nausea, blurred vision (e.g., seeing spots), shakiness, numb lips and/or tongue, irritability, fainting, clammy skin, confusion, nervousness, weakness, and/or rapid heart beat.

As used herein, the term "insulin drug" refers to any molecule capable of eliciting one or more biological responses associated with insulin (e.g., regulation of glucose homeostasis in target tissues such as the liver, muscle and/or fat, stimulation of cellular utilization and storage of glucose, amino acids, and/or fatty acids, and inhibition of catabolic processes such as the breakdown of glycogen, fat and protein) including, but not limited to, insulin polypeptides such as insulin, insulin analogs, active insulin fragments, and active insulin fragment analogs, insulin polypeptide derivatives, and insulin agonist molecules, mixtures thereof or pharmaceutical compositions comprising such molecules or mixtures of such molecules.

As used herein, the term "insulin" means the insulin of any of various species, as will be understood by those skilled in the art, such as one of the following species: human, cow, pig, sheep, horse, dog, chicken, duck or whale, provided by natural, synthetic, or genetically engineered sources. In various embodiments of the present invention, insulin is preferably human insulin.

As used herein, the term "insulin analog" means insulin wherein one or more of the amino acids have been replaced while retaining some or all of the activity of the insulin. The analog is described by noting the replacement amino acids with the position of the replacement as a superscript followed by a description of the insulin. For example, "$\text{Arg}^{B29}$ insulin, human" means that the lysine typically found at the B29 position of a human insulin molecule has been replaced with arginine.

Insulin analogs may be obtained by various means, as will be understood by those skilled in the art. For example, certain amino acids may be substituted for other amino acids in the insulin structure without appreciable loss of interactive binding capacity with structures such as, for example, antigen-binding regions of antibodies or binding sites on substrate molecules. As the interactive capacity and nature of insulin defines its biological functional activity, certain amino acid sequence substitutions can be made in the amino acid sequence and nevertheless remain a polypeptide with like properties.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporated herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As will be understood by those skilled in the art, insulin analogs may be prepared by a variety of recognized peptide synthesis techniques including, but not limited to, classical (solution) methods, solid phase methods, semi-synthetic methods, and recombinant DNA methods.

Examples of human insulin analogs include, but are not limited to, $\text{Gly}^{A21}$ insulin, human; $\text{Gly}^{A21}$ $\text{Gln}^{B3}$ insulin, human; $\text{Ala}^{A21}$ insulin, human; $\text{Ala}^{A21}$ $\text{Gln}^{B3}$ insulin, human; $\text{Gln}^{B3}$ insulin, human; $\text{Gln}^{B30}$ insulin, human; $\text{Gly}^{A21}$ $\text{Glu}^{B30}$ insulin, human; $\text{Gly}^{A21}$ $\text{Gln}^{B3}$ $\text{Glu}^{B30}$ insulin, human; $\text{Gln}^{B3}$ $\text{Glu}^{B30}$ insulin, human; $\text{Asp}^{B28}$ insulin, human; $\text{Lys}^{B28}$ insulin, human; $\text{Leu}^{B28}$ insulin, human; $\text{Val}^{B28}$ insulin, human; $\text{Ala}^{B28}$ insulin, human; $\text{Asp}^{B28}$ $\text{Pro}^{B29}$ insulin, human; $\text{Lys}^{B28}$ $\text{Pro}^{B29}$ insulin, human; $\text{Leu}^{B28}$ $\text{Pro}^{B29}$ insulin, human; $\text{Val}^{B28}$ $\text{Pro}^{B29}$ insulin, human; $\text{Ala}^{B28}$ $\text{Pro}^{B29}$ insulin, human.

As used herein, the term "active insulin fragment" means a segment of the amino acid sequence found in the insulin that retains some or all of the activity of the insulin. Insulin fragments are denoted by stating the position(s) in an amino acid sequence followed by a description of the amino acid. For example, a "B25-B30 human insulin" fragment would be the six amino acid sequence corresponding to the B25, B26, B27, B28, B29 and B30 positions in the human insulin amino acid sequence.

As used herein, the term "active insulin fragment analog" means a segment of the amino acid sequence found in the insulin molecule wherein one or more of the amino acids in the segment have been replace while retaining some or all of the activity of the insulin.

As used herein, an "insulin drug of this invention" includes any insulin polypeptide such as insulin, an insulin analog, an active insulin fragment, or an active insulin fragment analog as described herein and which can be conjugated to the various moieties of this invention.

As used herein, "insulin polypeptide derivative" refers to an insulin polypeptide such as insulin, an insulin analog, an active insulin fragment, or an active insulin fragment analog that has been conjugated to one or more moieties, such as acyl moieties (e.g., fatty acids) and/or oligomers, that improve the lipophilicity and/or hydrophilicity of the insulin polypeptide such that the insulin polypeptide conjugate is more lipophilic and/or more hydrophilic than the corresponding unconjugated insulin polypeptide. The hydrophilicity of an insulin polypeptide derivative can be compared to the hydrophilicity of the unconjugated insulin polypeptide by various means as will be understood by those skilled in the art. For example, a given amount of the insulin polypeptide derivative can be added to water, and the resulting solution can be mixed and filtered. The filtrate can be analyzed using known HPLC methods to determine the amount of conjugate present in the filtrate, and, thus, the amount of conjugate dissolved in the water. Alternatively, the filter paper can be weighed before and after filtration to determine the weight of conjugate not dissolved in the water. This weight can be used to determine the concentration of conjugate in the water. The same procedure can be repeated using the unconjugated insulin polypeptide and the two concentrations can be compared. The molecule that produces the higher concentration in water is considered to be the more hydrophilic molecule. The lipophilicity of an insulin polypeptide derivative can be compared to the lipophilicity of the unconjugated insulin polypeptide by various means as will be understood by those skilled in the art. For example, a given amount of the insulin polypeptide derivative can be analyzed by reverse phase HPLC as will be understood by those skilled in the art. The unconjugated insulin polypeptide can be analyzed using the same reverse phase HPLC method, and the elution times of the insulin polypeptide derivative and the unconjugated insulin polypeptide can be compared. The molecule with the longer elution time is considered to be the more lipophilic molecule.

As used herein, the term "amphiphilically balanced insulin polypeptide-oligomer conjugate" refers to a conjugate that is both more lipophilic than the unconjugated insulin polypeptide and more hydrophilic than the unconjugated insulin polypeptide. One skilled in the art will understand how to determine if an insulin polypeptide-oligomer conjugate is amphiphilically balanced. For example, a given amount of the insulin polypeptide-oligomer conjugate can be added to water, and the resulting solution can be mixed and filtered. The filtrate can be analyzed using known HPLC methods to determine the amount of conjugate present in the filtrate, and, thus, the amount of conjugate dissolved in the water. Alternatively, the filter paper can be weighed before and after filtration to determine the weight of conjugate not dissolved in the water. This weight can be used to determine the concentration of conjugate in the water. The concentration of insulin polypeptide-oligomer conjugate in the water should be greater than the concentration in water of unconjugated insulin polypeptide determined utilizing the same procedure. A given amount of the insulin polypeptide-oligomer conjugate can then be analyzed by reverse phase HPLC as will be understood by those skilled in the art. The elution time of the insulin polypeptide-oligomer conjugate should be greater than the elution time of the unconjugated insulin polypeptide.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—$CH_2$—$CH_2$—O—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

As used herein, phrases such as "between X and Y" should be interpreted to include X and Y.

As used herein, phrases such as "between about X and Y" mean "between about X and about Y" and phrases such as "from about X to Y" mean "from about X to about Y."

As used herein, the terms "ester moiety", "thio-ester moiety", "carbamate moiety", "ether moiety", "thio-carbamate moiety", "carbonate moiety", "thio-carbonate moieties", "urea moiety" and "amide moiety" are used to refer to the named moiety, in any of its various possible orientations. The moiety may include one or two lower alkylene moieties in addition to the named moiety. For example, the term "ester moiety" refers to a —O—C(O)— moiety, a —C(O)—O— moiety, or either of these moieties having a lower alkylene moiety at one or both ends of the moiety.

According to embodiments of the present invention, a method for reducing hypoglycemic episodes experienced by a subject in need of treatment for diabetes mellitus includes orally administering an effective amount of an insulin drug of this invention to the subject thereby reducing the number and/or severity of hypoglycemic episodes experienced by the subject during a given time period when compared with the number and/or severity of hypoglycemic episodes that would have been experienced by the subject during a similar time period to obtain an equivalent level or a substantially equivalent level of glycemic control utilizing parenteral administration of insulin or an insulin analog.

This invention also provides a method for reducing hypoglycemic episodes experienced by a subject in need of treatment for diabetes mellitus, said method comprising orally administering an amount of an insulin polypeptide-oligomer conjugate to the subject, wherein: i) the amount of the insulin polypeptide-oligomer conjugate reduces the number and/or severity of hypoglycemic episodes experienced by the subject during a given time period when compared with the number and/or severity of hypoglycemic episodes that would have been experienced during a similar time period by subjects in a control group parenterally administered insulin or an insulin analog in an amount that provides an equivalent or a substantially equivalent level of glycemic control; and ii) the oligomer of the insulin polypeptide-oligomer conjugate comprises a hydrophilic moiety and a lipophilic moiety.

A method is additionally provided for reducing hypoglycemic episodes experienced by a subject in need of treatment for diabetes mellitus, said method comprising orally administering an amount of an insulin polypeptide-oligomer conjugate to the subject, wherein: i) the amount of the insulin polypeptide-oligomer conjugate reduces the number and/or severity of hypoglycemic episodes experienced by the subject during a given time period when compared with the number and/or severity of hypoglycemic episodes that would have been experienced during a similar time period by the subject parenterally administered insulin or an insulin analog in an amount that provides an equivalent or substantially equivalent level of glycemic control; and ii) the oligomer of the insulin polypeptide-oligomer conjugate comprises a hydrophilic moiety and a lipophilic moiety.

The time period during which the hypoglycemic episodes can be counted and/or evaluated for degree of severity can be the time period of a single dose, or an extended treatment time period, e.g., number/severity of hypoglycemic episodes over hours, days, weeks and/or months. A reduction in the number of hypoglycemic episodes is readily determined by one skilled in the art by identifying and quantitating the number of hypoglycemic episodes a subject experiences within a given time period. A reduction in the severity of hypoglycemic episodes is readily determined by one of ordinary skill in the art by evaluating well known and art-recognized clinical signs and symptoms and the clinical profile of a hypoglycemic episode and as described herein and identifying a modulation of these signs and symptoms and/or other clinical parameters to determine that the severity of the hypoglycemic episodes experienced by a subject is reduced (see, e.g., Higgins. "Diagnosing diabetes: blood glucose and the role of the laboratory" *Br. J. Nurs.* 10:230-236 (2001), the entire contents of which are incorporated by reference herein).

As used in various embodiments herein, a level of glycemic control can be achieved when blood glucose is maintained in a subject between about 70 and 120 mg/dl before meals and less than about 180 mg/dl after meals. An equivalent or substantially equivalent level of glycemic control includes a level of glycemic control wherein blood glucose is maintained in a subject between about 70 and 120 mg/dl before meals and less than about 180 mg/dl after meals with a tolerance of ±5%, 10%, 15% or 20% of these values.

According to other embodiments of the present invention, a method for providing tight control of blood glucose in a subject in need of treatment for diabetes mellitus includes orally administering an effective amount of an insulin drug of this invention to the subject to provide tight control of blood glucose in the subject. That tight control of blood glucose is achieved in the subject can be readily determined by one of ordinary skill in the art employing standard methods of determining blood glucose levels. In one embodiment of this invention, the method is directed to improving the ability to maintain tight control of blood glucose in a subject by orally administered an insulin drug of this invention to the subject, wherein the improvement is determined by a comparison of the ability of the subject, or of a control group, to maintain tight control of blood glucose when parenterally administered insulin.

According to still other embodiments of the present invention, a method for controlling blood glucose between about 70 and 120 mg/dl before meals and less than about 180 mg/dl after meals in a subject in need of treatment for diabetes mellitus includes orally administering an effective amount of an insulin drug of this invention to the subject to control blood glucose in the subject between about 70 and 120 mg/dl before meals and less than about 180 mg/dl after meals. That blood glucose levels in the subject are maintained as described can be readily determined by one of ordinary skill in the art employing standard methods of determining blood glucose levels. In one embodiment of this invention, the method is directed to improving the ability to control blood glucose between about 70 and 120 mg/dl before meals and less than about 180 mg/dl after meals in a subject by orally administered an insulin drug of this invention to the subject, wherein the improvement is determined by a comparison of the ability of the subject, or of a control group, to control blood glucose in the subject between about 70 and 120 mg/dl before meals and less than about 180 mg/dl after meals when parenterally administered insulin.

According to yet other embodiments of the present invention, a method for maintaining a glycated hemogloblin level of less than about 7 percent in a subject in need of treatment for diabetes mellitus includes orally administering an effective amount of an insulin drug of this invention to the subject to maintain a glycated hemoglobin level in the subject of less than about 7 percent. That glycated hemoglobin levels in the subject are maintained as described can be readily determined by one of ordinary skill in the art employing standard methods of determining glycated hemoglobin levels (see, e.g., Harmel et al. "Glycohemoglobin assessment program: glycated hemoglobin and epidemiologic variables in patients with type 2 diabetes" *Endocr. Pract.* 8:184-190 (2002), the entire contents of which are incorporated by reference herein). In one embodiment of this invention, the method is directed to improving the ability to maintain a glycated hemoglobin level in a subject by orally administered an insulin drug of this invention to the subject, wherein the improvement is determined by a comparison of the ability of the subject, or of a control group, to maintain a glycated hemoglobin level when parenterally administered insulin.

According to other embodiments of the present invention, a method for reducing low blood glucose reactions in a subject having a tendency to experience low blood glucose reactions following parenteral administration of insulin or an insulin analog includes orally administering an effective amount of an insulin drug of this invention to the subject thereby reducing the number of low blood glucose reactions experienced by the subject. That low blood glucose reactions in the subject are reduced can be readily determined by one of ordinary skill in the art employing standard methods of identifying and quantitating blood glucose levels and low blood glucose reactions. In one embodiment of this invention, the method is directed to improving the ability to reduce the number of low blood glucose reactions experienced by the subject orally administered an insulin drug of this invention to the subject, wherein the improvement is determined by a comparison of the ability to reduce the number of low blood glucose reactions experienced by the subject, or by a control group, when parenterally administered insulin.

By utilizing methods according to embodiments of the present invention, the number of hypoglycemic episodes experienced by the subject can be reduced by at least 1, 2, 3, 4, 5, 6 or more episodes in a 12-, 24-, 36-, 48-, 60-, or 72-hour period.

By utilizing methods according to embodiments of the present invention, the severity of hypoglycemic episodes experienced by the subject can be reduced by at least about 5, 10, 15, 20, 25, 30, 35, 40, 45, 50, 55, 60 percent or more. As used in various embodiments herein, the severity of a hypoglycemic episode can be determined by measuring the blood glucose level of a subject, with a lower blood glucose level being more severe. The severity of two hypoglycemic episodes are compared using the following formula:

$$\text{Percent Reduction in Severity} = \frac{BGL1 - BGL2}{80 - BGL2} \times 100$$

where $BGL1$=blood glucose level$_1$ expressed in mg/dL;
$BGL2$=blood glucose level$_2$ expressed in mg/dL;
BGL2 is the lower of BGL1 and BGL2; and
BLG1 and BLG2 are measured at the same time following or preceding a glucose-producing event (e.g., a meal).

Thus, for example, if blood glucose level$_1$ is 55 mg/dL and blood glucose level$_2$ is 50 mg/dl, the percent reduction in severity achieved by employing the method that resulted in blood glucose level$_1$ when compared to the method that resulted in blood glucose level$_2$ is roughly 17%.

The subject of this invention can be any subject in need of treatment for diabetes mellitus including, but not limited to, mammalian subjects. The subject is most preferably a human subject. The subject of the methods of this invention also includes a subject having a tendency to experience low blood glucose reactions, a subject 12 years of age or younger, a subject 65 years of age or older, a subject who has coronary heart disease, a subject who has end-stage kidney disease, a subject with severe vision loss as a complication resulting from diabetes mellitus and a subject who has any combination of these conditions The effective amount of insulin drug is preferably between a lower limit of about 0.05, 0.06, 0.07, 0.08, 0.09, 0.1, 0.11, 0.12, 0.125, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.125, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, or 2 mg per kilogram of patient body weight and an upper limit of about 0.06, 0.07, 0.08, 0.09, 0.1, 0.11, 0.12, 0.125, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.125, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, 2, 2.5, 3, 3.5, 4, 4.5, 5, 5.5, 6, 6.5, 7, 7.5, 8, 8.5, 9, 9.5, or 10 mg per kilogram of patient body weight. More preferably, the effective amount of insulin drug is between about 0.1 and 1 mg per kilogram of patient body weight.

Oral administration of the insulin drug can occur at various times during the day. The insulin drug is preferably administered at or near (e.g., within one hour of) meal time. In embodiments of the present invention, the insulin drug is administered less than about one hour before ingesting a meal. The insulin drug is preferably administered less than about 30 minutes prior to ingesting a meal, and is more preferably administered less than about 20 minutes prior to ingesting a meal. In other embodiments of the present invention, the insulin drug is administered within about two hours after ingesting a meal, is preferably administered less than one hour after ingesting a meal, and is more preferably administered less than about 30 minutes after ingesting a meal. In still other embodiments, the insulin drug is administered contemporaneously with ingesting a meal. Insulin drug administered contemporaneously with ingesting the meal may be less preferred because it may require higher dosages and result in dose-to-dose variability for a given patient.

Administration of the insulin drug may occur before one or more meals per day. Additionally, the insulin drug may be administered at various times in addition to a meal time, for example, before retiring for four or more hours of sleep (e.g., going to bed at night) and/or upon waking up from four or more hours of sleep (e.g., waking up in the morning). Administration of insulin drug according to methods of the present invention prior to retiring for four or more hours of sleep may provide effective glucose homeostasis throughout all or a portion of the period of sleep, preventing or reducing the likelihood of the Dawn Phenomenon, which typically occurs in individuals with Type 1 diabetes mellitus and is characterized by a hypoglycemic episode occurring during a period of sleep.

In other embodiments according to the present invention, methods of reducing the hypoglycemic episodes experienced by a subject in need of treatment for diabetes mellitus include orally administering an effective amount of a first insulin drug to the subject as described in the various embodiments above and administering an effective amount of a second insulin drug to the peripheral system of the patient. Preferably, the peripheral administration is performed by parenteral injection of an intermediate or long-acting insulin and provides basal levels of insulin. The total daily dosage of intermediate or long-acting insulin may range from 2 to 100 units per day and may be administered in one or divided in two or more doses per day. More preferably, the peripheral administration is performed by continuous subcutaneous insulin injection (CSII), as will be understood by those skilled in the art. The CSII dosage is preferably selected to provide a basal level of insulin in the body. The CSII dosage may be between a lower limit of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, or 2.9 Units (U) per hour and an upper limit of about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 Units (U) per hour, and is preferably between about 0.5 and 1.5 U/hour. The first and second insulin drugs may be the same or different.

The insulin drug of the above-described embodiments is preferably an insulin polypeptide derivative. The insulin polypeptide derivative is preferably an acylated insulin polypeptide or an insulin polypeptide-oligomer conjugate. Acylated insulin polypeptides are insulin polypeptides that have been derivatized with one or more acyl-containing moieties, such as fatty acid moieties and/or arylacyl moieties. The fatty acid moiety may be a saturated or unsaturated, linear or branched fatty acid moiety such as, but not limited to, caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic, linolenic, arachidic, and arachidonic acid, or a fatty acid derivative such as an aryl-fatty acid derivative (e.g., phenylacetyl) or a cycloalkyl-fatty acid derivative (e.g., cyclohexylacetyl or cyclohexylpropionyl). Arylacyl moieties include, but are not limited to, benzoyl. The insulin polypeptide-oligomer conjugate is an insulin polypeptide conjugated with an oligomer, such as a polyalkylene glycol moiety or a polyalkylene glycol-containing moiety. Insulin polypeptide derivatives according to embodiments of the present invention may be synthesized using methods that are known to those skilled in the art.

According to embodiments of the present invention, the insulin polypeptide-oligomer conjugate is an amphiphilically balanced insulin polypeptide-oligomer conjugate. The amphiphilically balanced insulin polypeptide-oligomer conjugate preferably comprises an insulin polypeptide coupled to an oligomer that comprises a hydrophilic moiety coupled to a lipophilic moiety. The insulin polypeptide is preferably insulin or an insulin analog. More preferably, the insulin polypeptide is human insulin or a human insulin analog. Still more preferably, the insulin polypeptide is human insulin. The hydrophilic moiety may be coupled to the lipophilic moiety by a hydrolyzable or a non-hydrolyzable bond, or there may be one or more intervening moieties that couple the hydrophilic moiety to the lipophilic moiety.

The hydrophilic moiety of the amphiphilically balanced insulin polypeptide-oligomer conjugate is a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

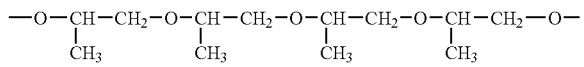

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The lipophilic moiety of the amphiphilic insulin polypeptide-oligomer conjugate is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22 carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, myristate, palmitate, stearate, arachidate, behenate, lignocerate, and cerotate.

The oligomer portion of the amphiphilically balanced insulin polypeptide-oligomer conjugate may comprise one or more other moieties as will be understood by those skilled in the art including, but not limited to, additional hydrophilic moieties, spacer moieties, linker moieties, and terminating moieties. The various moieties in the oligomer are covalently coupled to one another by either hydrolyzable or non-hydrolyzable bonds.

The oligomer portion of the amphiphilically balanced insulin polypeptide-oligomer conjugate may comprise one or more additional hydrophilic moieties (i.e., moieties in addition to the hydrophilic moiety) including, but not limited to, sugars, polyalkylene glycols, and polyamine/PEG copolymers. Adjacent polyalkylene glycol moieties will be considered to be the same moiety if they are coupled by ether bonds. For example, the moiety

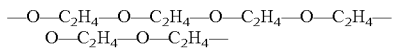

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

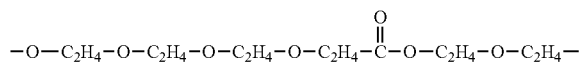

is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer portion of the amphiphilically balanced insulin polypeptide-oligomer conjugate may comprise one or more spacer moieties as will be understood by those skilled in the art. Spacer moieties may, for example, be used to separate a hydrophilic moiety from a lipophilic moiety, to separate a lipophilic moiety or hydrophilic moiety from the insulin polypeptide, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer portion of the amphiphilically balanced insulin polypeptide-oligomer conjugate may comprise one or more linker moieties that are used to couple the oligomer with the insulin polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

The oligomer portion of the amphiphilically balanced insulin polypeptide-oligomer conjugate may comprise one or more terminating moieties at the one or more ends of the oligomer, which are not coupled to the insulin polypeptide. The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to other embodiments of the present invention, the insulin drug administered according to the methods of reducing hypoglycemic events in a subject in need of treatment for diabetes mellitus described above is an insulin polypeptide-oligomer conjugate comprising the structure of Formula I:

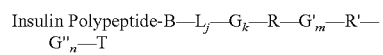

wherein:

B is a bonding moiety;

L is a linker moiety;

G, G' and G" are individually selected spacer moieties;

R is a lipophilic moiety and R' is a polyalkylene glycol moiety, or R' is the lipophilic moiety and R is the polyalkylene glycol moiety;

T is a terminating moiety; and j, k, m and n are individually 0 or 1.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula I is preferably an amphiphilically balanced insulin polypeptide-oligomer conjugate.

According to these embodiments of the present invention, the polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

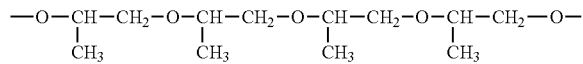

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22 carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaenoate, and docosahexaenoate; and saturated fatty acid moieties such as acetate, caproate, caprylate, caprate, laurate, myristate, palmitate, stearate, arachidate, behenate, lignocerate, and cerotate.

According to these embodiments of the present invention, the spacer moieties, G, G' and G", are spacer moieties as will be understood by those skilled in the art. Spacer moieties are preferably selected from the group consisting of sugar moieties, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms. Preferably, oligomers of these embodiments do not include spacer moieties (i.e., k, m and n are preferably 0).

According to these embodiments of the present invention, the bonding moiety, B, may be various bonding moieties as will be understood by those skilled in the art including, but not limited to, an ester moiety, a thio-ester moiety, an ether moiety, a carbamate moiety, a thio-carbamate moiety, a carbonate moiety, a thio-carbonate moiety, an amide moiety, a urea moiety, and a covalent bond. When the bonding moiety is a carbamate moiety or an amide moiety, the nitrogen portion of the moiety is preferably provided by an amino moiety of the insulin polypeptide, such as the ε-amino moiety at the $Lys^{B29}$ position of human insulin. The bonding moiety is preferably an ester moiety, an ether moiety, a carbamate moiety, a carbonate moiety, an amide moiety, or a covalent bond. The bonding moiety is more preferably an ester moiety, a carbamate moiety, a carbonate moiety, or an amide moiety. The bonding moiety is still more preferably an amide moiety having the nitrogen portion of the amide moiety provided by an amino moiety of the insulin polypeptide.

According to these embodiments of the present invention, the linker moiety, L, may be various linker moieties as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

According to these embodiments of the present invention, the terminating moiety, T, is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugar moieties, cholesterol, alcohols, and fatty acid moieties.

In still other embodiments, the insulin drug administered according to the methods of reducing hypoglycemic episodes experienced by a subject in need of treatment for diabetes mellitus described above is an insulin polypeptide-oligomer conjugate comprising the structure of Formula II:

Insulin polypeptide-X(CH$_2$)$_m$Y(C$_2$H$_4$O)$_n$R    (II)

wherein:

X is an ester moiety, a thio-ester moiety, an ether moiety, a carbamate moiety, a thio-carbamate moiety, a carbonate moiety, a thio-carbonate moiety, an amide moiety, a urea moiety or a covalent bond; is preferably an ester moiety, an ether moiety, a carbamate moiety, a carbonate moiety, an amide moiety, or a covalent bond; is more preferably an ester moiety, a carbamate moiety, a carbonate moiety, or an amide moiety; and is still more preferably an amide moiety. When X is an amide moiety or a carbamate moiety, an amino group of the insulin polypeptide is preferably the nitrogen portion of the amide or carbamate moiety;

Y is an ester moiety, a thio-ester moiety, an ether moiety, a carbamate moiety, a thio-carbamate moiety, a carbonate moiety, a thio-carbonate moiety, an amide moiety, a urea moiety or a covalent bond, is preferably an ester moiety, an ether moiety, a carbamate moiety, a carbonate moiety, an amide moiety, or a covalent bond; is more preferably an ester moiety, an ether, a carbamate moiety, a carbonate moiety, or an amide moiety; and is still more preferably an ether moiety.

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a C$_1$ to C$_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula II is preferably an amphiphilically balanced insulin polypeptide-oligomer conjugate.

In still other embodiments, the insulin drug administered according to the methods of reducing hypoglycemic episodes experienced by a subject in need of treatment for diabetes mellitus described above is an insulin polypeptide-oligomer conjugate comprising the structure of Formula III:

Insulin polypeptide-X(CH$_2$)$_m$(OC$_2$H$_4$)$_n$OR    (III)

wherein:

X is an ester moiety, a thio-ester moiety, an ether moiety, a carbamate moiety, a thio-carbamate moiety, a carbonate moiety, a thio-carbonate moiety, an amide moiety, a urea moiety or a covalent bond; is preferably an ester moiety, an ether moiety, a carbamate moiety, a carbonate moiety, an amide moiety, or a covalent bond; is more preferably an ester moiety, a carbamate moiety, a carbonate moiety, or an amide moiety; and is still more preferably an amide moiety. When X is an amide moiety or a carbamate moiety, an amino group of the insulin polypeptide is preferably the nitrogen portion of the amide or carbamate moiety.

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a C$_1$ to C$_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula III is preferably an amphiphilically balanced insulin polypeptide-oligomer conjugate.

In yet other embodiments, the insulin drug administered according to the methods of reducing hypoglycemic episodes experienced by a subject in need of treatment for diabetes mellitus described above is an insulin polypeptide-oligomer conjugate comprising the structure of Formula IV:

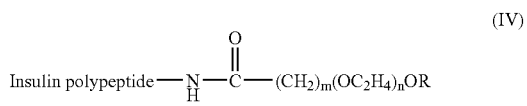

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, myristate, palmitate, stearate, arachidate, behenate, lignocerate, and cerotate. The sugar moiety may be various sugar moieties as will be understood by those skilled in the art. Likewise, the alcohol moiety may be various alcohol moieties as will be understood by those skilled in the art.

According to these embodiments of the present invention, the insulin polypeptide is preferably insulin or an insulin analog. More preferably, the insulin polypeptide is human insulin or a human insulin analog, and, still more preferably, the insulin polypeptide is human insulin. The insulin polypeptide-oligomer conjugate of Formula IV is preferably an amphiphilically balanced insulin polypeptide-oligomer conjugate.

In still other embodiments, the insulin drug administered according to the methods of reducing hypoglycemic episodes experienced by a subject in need of treatment for diabetes mellitus described above is an insulin polypeptide-oligomer conjugate comprising the structure of Formula V:

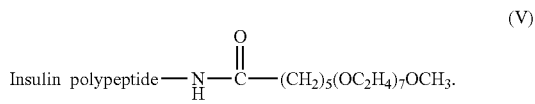

According to these embodiments of the present invention, the insulin polypeptide is preferably insulin or an insulin analog. More preferably, the insulin polypeptide is human insulin or a human insulin analog, and, still more preferably, the insulin polypeptide is human insulin. When the insulin polypeptide in the structure of Formula V is human insulin and the oligomer is conjugated to the B29 lysine of the human insulin, this insulin-oligomer conjugate is referred to herein as HIM2. HIM2 is a polydispersed mixture of insulin-oligomer conjugates. It may be still more preferable to use a substantially monodispersed or monodispersed mixture of insulin-oligomer conjugates as described in U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same," the disclosure of which is incorporated herein in its entirety. The insulin polypeptide-oligomer conjugate of Formula V is amphiphilically balanced when the insulin polypeptide is insulin.

HIM2 may be synthesized by various methods as will be understood by those skilled in the art. HIM2 is preferably synthesized utilizing proinsulin as a starting material as described in U.S. patent application Ser. No. 10/036,744 filed Dec. 21, 2001 by Soltero et al. entitled "Methods of Synthesizing Insulin Polypeptide-Oligomer Conjugates, and Proinsulin Polypeptide-Oligomer Conjugates and Methods of Synthesizing Same," the disclosure of which is incorporated herein in its entirety. For example, HIM2 has been synthesized as follows. Recombinant proinsulin having a leader peptide (MW 10,642 Daltons) was obtained from Biobras, of Belo Horizonte, Brazil. A $2.32 \times 10^{-3}$ mmol portion of the proinsulin was dissolved in 10 mL of DMSO. To the solution was added 324 μL of triethylamine. The resulting solution was allowed to stir for 5 minutes, and then a solution of activated methylheptaethylene glycol ((PEG7)-hexyl oligomer) ($9.30 \times 10^{-3}$ mmol) in acetonitrile was added. The course of the conjugation (acylation) reaction was monitored by HPLC. When reaction appeared to be complete, it was quenched by addition of 3.54 mL of 5% aqueous trifluoroacetic acid solution. The reaction mixture was then processed and exchanged into 100 mM Tris-HCl Buffer, pH 7.6 to provide a product mixture. An aliquot of the Tris-HCl solution of the product mixture was analyzed by HPLC to determine the polypeptide concentration. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.424 μmol/mL) was then allowed to react with trypsin ($5.97 \times 10^{-4}$ μmol/mL) and carboxypeptidase B ($1.93 \times 10^{-4}$ μmol/mL). After 30 minutes, the reaction was quenched by the addition of 1.58 mL of 1% trifluoroacetic acid in acetonitrile. The major products were identified by HPLC retention time (relative to the retention times of known reference standards) and mass spectral analysis. Insulin (10%) and $Lys^{B29}$-Hexyl-PEG7-Oligomer-Conjugated Insulin (84%) were thus obtained.

In the various embodiments of insulin polypeptide-oligomer conjugates described above, the oligomer is covalently coupled to the insulin polypeptide. In some embodiments, the oligomer is coupled to the insulin polypeptide utilizing a hydrolyzable bond (e.g., an ester or carbonate bond). A hydrolyzable coupling may provide an insulin polypeptide-oligomer conjugate that acts as a prodrug. In other embodiments, the oligomer is coupled to the insulin polypeptide utilizing a non-hydrolyzable bond (e.g., a carbamate, amide, or ether bond).

In the various embodiments of insulin polypeptide-oligomer conjugates described above, more than one oligomer (i.e., a plurality of oligomers) may be coupled to the insulin polypeptide. The oligomers in the plurality are preferably the same. However, it is to be understood that the oligomers in the plurality may be different from one another, or, alternatively, some of the oligomers in the plurality may be the same and some may be different. When a plurality of oligomers are coupled to the insulin polypeptide, it may be preferable to couple one or more of the oligomers to the insulin polypeptide with hydrolyzable bonds and couple one or more of the oligomers to the insulin polypeptide with non-hydrolyzable bonds. Alternatively, all of the bonds coupling the plurality of oligomers to the insulin polypeptide may be hydrolyzable, but have varying degrees of hydrolyzability such that, for example, one or more of the oligomers is rapidly removed from the insulin polypeptide by hydrolysis in the body and one or more of the oligomers is slowly removed from the insulin polypeptide by hydrolysis in the body.

In the various embodiments of insulin polypeptide-oligomer conjugates described above, the oligomer may be coupled to the insulin polypeptide at various nucleophilic residues of the insulin polypeptide including, but not limited to, nucleophilic hydroxyl functions and/or amino functions. A nucleophilic hydroxyl function may be found, for example, at serine and/or tyrosine residues, and/or at one or more of C-termini of the polypeptide. A nucleophilic amino function may be found, for example, at histidine and/or lysine residues, and/or at the one or more N-termini of the polypeptide.

When an oligomer is coupled to the one or more N-termini of the insulin polypeptide, the coupling preferably forms a secondary amine. When the insulin drug is human insulin, for example, the oligomer may be coupled to an amino functionality of the insulin, including the amino functionality of $Gly^{A1}$, the amino functionality of $Phe^{B1}$, and the amino functionality of $Lys^{B29}$. When one oligomer is coupled to the human insulin, the oligomer is preferably coupled to the amino functionality of $Lys^{B29}$. When two oligomers are coupled to the human insulin, the oligomers are preferably coupled to the amino functionality of $Phe^{B1}$ and the amino functionality of $Lys^{B29}$. While more than one oligomer may be coupled to the human insulin, a higher activity (improved glucose lowering ability) is observed for the mono-conjugated human insulin.

The insulin polypeptide-oligomer conjugates employed in the various embodiments described above may be synthesized by various methods as will be understood by those skilled in the art. For example, polydispersed insulin polypeptide-oligomer conjugates may be synthesized by the methods provided in one or more of the following references: U.S. Pat. No. 5,359,030 to Ekwuribe; U.S. Pat. No. 5,438,040 to Ekwuribe; U.S. Pat. No. 5,681,811 to Ekwuribe; U.S. Pat. No. 6,309,633 to Ekwuribe et al.; and U.S. patent application Ser. No. 10/036,744 filed Dec. 21, 2001 by Soltero et al. entitled "Methods of Synthesizing Insulin Polypeptide-Oligomer Conjugates, and Proinsulin Polypeptide-Oligomer Conjugates and Methods of Synthesizing Same", the disclosures of which are incorporated herein by reference in their entireties. Non-polydispersed (e.g., substantially monodispersed and monodispersed) insulin polypeptide-oligomer conjugates may be synthesized by methods provided in one or more of the following references: U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same"; and U.S. patent application Ser. No. 10/036,744 filed Dec. 21, 2001 by Soltero et al. entitled "Methods of Synthesizing Insulin Polypeptide-Oligomer Conjugates, and Proinsulin Polypeptide-Oligomer Conjugates and Methods of Synthesizing Same", the disclosures of which are incorporated herein by reference in their entireties. Oligomers according to embodiments of the present invention are preferably substantially monodispersed and are more preferably monodispersed.

A monodispersed mixture of insulin polypeptide-oligomer conjugates may be synthesized, for example, utilizing methods described in U.S. Pat. No. 5,359,030 to Ekwuribe; U.S. Pat. No. 5,438,040 to Ekwuribe; U.S. Pat. No. 5,681,811 to Ekwuribe; or U.S. Pat. No. 6,309,633 to Ekwuribe et al. by using a monodispersed polyethylene glycol (PEG) mixture as a starting material. Such monodispersed PEG mixtures may be provided, for example, by methods described in Yiyan Chen & Gregory L. Baker, *Synthesis and Properties of ABA Amphiphiles*, 64 *J. Org. Chem.* 6870-6873 (1999) and in Gérard Coudert et al., *A Novel, Unequivocal Synthesis of Polyethylene Glycols, Synthetic Communications,* 16(1): 19-26 (1986). A preferred method of synthesizing monodispersed PEG mixtures to be utilized in forming monodispersed mixtures of insulin polypeptide-oligomer conjugates is described in U.S. patent application Ser. No. 09/873,371 to Ekwuribe et al. entitled "Methods of Synthesizing Substantially Monodispersed Mixtures of Polymers Having Polyethylene Glycol Moieties," the disclosure of which is incorporated herein in its entirety. An exemplary synthesis route includes reacting a monodispersed mixture of compounds having the structure of Formula I:

$$R^1(OC_2H_4)_n-O^-X^+ \qquad (I)$$

wherein $R^1$ is H or a lipophilic moiety; n is from 1 to 25; and $X^+$ is a positive ion, with a monodispersed mixture of compounds having the structure of Formula II:

$$R^2(OC_2H_4)_m-OMS \qquad (II)$$

wherein $R^2$ is H or a lipophilic moiety; and m is from 1 to 25, under conditions sufficient to provide a monodispersed mixture of polymers comprising polyethylene glycol moieties and having the structure of Formula III:

$$R^2(OC_2H_4)_{m+n}-OR^1 \qquad (III).$$

The methods according to embodiments of the invention described above can be carried out utilizing a pharmaceutical composition comprising an insulin drug as described above and a pharmaceutical carrier. The carrier must, of course, be acceptable in the sense of being compatible with any other ingredients in the pharmaceutical composition and should not be deleterious to the subject. The carrier may be a solid or a liquid, or both, and is preferably formulated with the insulin drug as a unit-dose formulation, for example, a tablet, which may contain from about 0.01% or 0.5% to about 95% or 99% by weight of the insulin drug. The pharmaceutical compositions may be prepared by any of the well-known techniques of pharmacy including, but not limited to, admixing the components, optionally including one or more accessory ingredients. See, e.g., Remington, *The Science And Practice of Pharmacy* (9th Ed. 1995).

Pharmaceutical compositions suitable for oral administration may be presented in discrete units, such as capsules, cachets, lozenges, or tablets, each containing a predetermined amount of the insulin drug; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the insulin drug and a suitable carrier (which may contain one or more accessory ingredients as noted above).

In addition to an insulin drug, solid pharmaceutical compositions for oral administration according to embodiments of methods of the present invention may comprise various other ingredients as will be understood by those skilled in the art including, but not limited to, one or more of the ingredients described in the *National Formulary* 19, pages 2404-2406 (2000), the disclosure of pages 2404 to 2406 being incorporated herein by reference in their entirety. For example, the solid pharmaceutical formulations may include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers that may be used encompass those that are known in the art and are useful in the manufacture of various dosage forms. If desired, the solid formulations may include other components such as bulking agents and/or granulating agents, and the like. Solid pharmaceutical compositions may be provided by various methods as will be understood by those skilled in the art.

Solid dosage units for oral administration according to embodiments of methods of the present invention may be prepared by various methods as will be understood by those skilled in the art. For example, the insulin drug may be mixed with a solid, pulverant carrier such as, for example, lactose, saccharose, sorbitol, mannitol, starch, amylopectin, cellulose derivatives or gelatin, as well as with an antifriction agent such as, for example, magnesium stearate, calcium stearate, and polyethylene glycol waxes. The mixture may then be pressed into tablets. Tablets for oral use may also be prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is pressed through a stainless steel sieve having a desired size. The layers of the mixture are then dried in controlled drying units for determined length of time to achieve a desired particle size and consistency. The granules of the dried mixture are sieved to remove any powder. To this mixture, disintegrating, antifriction, and anti-adhesive agents are added. Finally, the mixture is pressed into tablets using a machine with the appropriate punches and dies to obtain the desired tablet size. The operating parameters of the machine may be selected by the skilled artisan.

If coated tablets are desired, the above prepared cores may be coated with a concentrated solution of sugar, which may contain gum arabic, gelatin, talc, titanium dioxide, or with a lacquer dissolved in volatile organic solvent or mixture of solvents. Additionally, coating may be carried out in aqueous or nonaqueous media using various excipients including, but not limited to, dispersed methylcellulose, dispersed ethylcellulose, dispersed methacrylates or mixtures thereof. To this coating various dyes may be added in order to distinguish among tablets with different active compounds or with different amounts of the active compound present.

Soft gelatin capsules may be prepared in which capsules contain a mixture of the active ingredient and a liquid, such as vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

Dry powder capsules may be made by various methods understood by those skilled in the art. An embodiment of a dry powder capsule that may be orally administered according to embodiments of the present invention is as follows:

| Component | % (w/w) |
| --- | --- |
| HIM2 | 1.11 |
| sodium cholate | 13.29 |
| capric acid | 5.13 |
| lauric acid | 5.13 |
| tris(hydroxymethy)aminomethane | 41.04 |

-continued

| Component | % (w/w) |
| --- | --- |
| sodium phosphate | 30.97 |
| sodium hydroxide | 1.03 |

Liquid pharmaceutical compositions that may be orally administered according to embodiments of methods of the present invention may be various liquid pharmaceutical compositions that include the insulin drug as an active ingredient as will be understood by those skilled in the art including, but not limited to, solutions or suspensions in aqueous or non-aqueous liquids such as those disclosed in U.S. Provisional Application No. 60/318,193 to Soltero et al., filed Sep. 7, 2001, entitled "Pharmaceutical Compositions," the disclosure of which is incorporated herein in its entirety, and oil-in-water or water-in-oil emulsions such as those disclosed in U.S. Pat. No. 6,191,105 to Ekwuribe et al., the disclosure of which is incorporated herein in its entirety. In addition to the active insulin drug, the liquid pharmaceutical formulation may comprise various ingredients including, but not limited to, absorption enhancers, buffering agents, polyhydric alcohols, polyalkylene oxides, and flavoring agents.

Absorption enhancers may be various absorption enhancers as will be understood by those skilled in the art including, but not limited to, bile acids such as, but not limited to, cholic acid, deoxycholic acid, ursodeoxycholic acid, lithocholic acid, and taurocholic acid and/or the pharmaceutically acceptable salts (e.g., earth metal salts) thereof, and fatty acids such as, but not limited to, caproic acid, caprylic acid, capric acid, undecanoic acid, lauric acid, tridecanoic acid, myristic acid, pentadecanoic acid, palmitic acid, heptadecanoic acid, stearic acid, oleic acid, elaidic acid, linoleic acid, linolenic acid, arachidic acid, arachidonic acid, and mixtures thereof.

Buffering agents may be various buffering agents as will be understood by those skilled in the art including, but not limited to, tris(hydroxymethyl)aminomethane, triethanolamine, sodium phosphate, citric acid, and mixtures thereof.

Polyhydric alcohols may be various polyhydric alcohols as will be understood by those skilled in the art including, but not limited to, glycerol. Polyalkylene glycols may be various polyalkylene glycols as will be understood by those skilled in the art including, but not limited to, polyethylene glycol and polypropylene glycol.

Flavoring agents may be various flavoring agents as will be understood by those skilled in the art including, but not limited to, natural or artificial flavors and sweeteners.

Embodiments of liquid pharmaceutical formulations that may be orally administered according to embodiments of methods of the present invention include the following:

| Component | Conc. | unit | % (w/v) |
| --- | --- | --- | --- |
| HIM2 | 2.5 | mg/ML | 0.25 |
| sodium cholate | 3 | % | 3.00 |
| oleic acid | 2 | % | 2.00 |
| tris(hydroxymethy)aminomethane | 250 | mM | 3.03 |
| sodium phosphate | 250 | mM | 3.00 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |

-continued

| Component | Conc. | unit | % (w/v) |
|---|---|---|---|
| oleic acid | 2 | % | 2.00 |
| tris(hydroxymethy)aminomethane | 500 | mM | 6.05 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 2 | % | 2.00 |
| tris(hydroxymethy)aminomethane | 250 | mM | 3.03 |
| triethanolamine | 250 | mM | 3.73 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 2 | % | 2.00 |
| citric acid | 500 | mM | 9.60 |
| triethanolamine | 250 | mM | 3.73 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 2 | % | 2.00 |
| citric acid | 500 | mM | 9.60 |
| tris(hydroxymethy)aminomethane | 250 | mM | 3.03 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 2 | % | 2.00 |
| citric acid | 500 | mM | 9.60 |
| sodium phosphate | 250 | mM | 3.00 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 2 | % | 2.00 |
| citric acid | 350 | mM | 6.72 |
| tris(hydroxymethy)aminomethane | 350 | mM | 4.24 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| lauric acid | 2 | % | 2.00 |
| citric acid | 350 | mM | 6.72 |
| triethanolamine | 350 | mM | 4.24 |
| sucralose | 0.2 | % | 0.20 |
| strawberry flavor | 0.4 | % | 0.4 |
| propylene glycol | 20 | % | 20.00 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 1 | % | 2.00 |
| capric acid | 0.5 | % | 0.50 |
| lauric acid | 0.5 | % | 0.50 |
| triethanolamine | 350 | mM | 5.22 |
| tris(hydroxymethy)aminomethane | 350 | mM | 4.24 |
| sodium phosphate | 350 | mM | 4.20 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 1 | % | 2.00 |
| capric acid | 0.5 | % | 0.5 |
| lauric acid | 0.5 | % | 0.5 |
| citric acid | 350 | mM | 6.72 |
| tris(hydroxymethy)aminomethane | 350 | mM | 4.24 |
| triethanolamine | 350 | mM | 5.22 |
| sucralose | 0.2 | % | 0.20 |
| strawberry flavor | 0.4 | % | 0.4 |
| sodium hydroxide | pH adjust to 7.8 | — | — |
| water | q.s. | — | — |
| HIM2 | 2.5 | mg/ML | 0.25 |
| sodium cholate | 3 | % | 3.00 |
| oleic acid | 1 | % | 2.00 |
| capric acid | 0.5 | % | 0.50 |
| lauric acid | 0.5 | % | 0.50 |
| citric acid | 175 | mM | 3.36 |
| triethanolamine | 350 | mM | 5.22 |
| tris(hydroxymethy)aminomethane | 350 | mM | 4.24 |
| sodium phosphate | 175 | mM | 4.20 |
| sucralose | 0.2 | % | 0.20 |
| strawberry flavor | 0.4 | % | 0.4 |
| sodium hydroxide | pH adjust to 7.8 | — | — |
| water | q.s. | — | — |

While the above-described embodiments of pharmaceutical formulations comprise HIM2 as an active ingredient, it is to be understood that the active ingredient could be various other insulin drugs described herein. The active ingredient is preferably an insulin polypeptide-oligomer conjugate as described above.

The present invention will now be described with reference to the following example. It should be appreciated that this example is for the purposes of illustrating aspects of the present invention, and does not limit the scope of the invention as defined by the claims.

EXAMPLE

Study Objectives: To evaluate whether HIM2 doses, when titrated, are able to maintain 2-hour post-prandial blood glucose levels consistent with the pre-study range between 80-250 mg/dL as compared to insulin lispro and to evaluate the safety profile for HIM2.

Patient Population: Adult patients with type 1 diabetes participated in the study. The patients had a BMI$\leq$29 kg/m$^2$, basal insulin using CSII therapy ($\leq$4 rate changes per, day), daily insulin requirements of less than 1 U/kg, HbA$_{1c}$ of less than 9%, and normal solid gastric emptying.

Design and Methods: A multicenter, dose titration, randomized, insulin lispro controlled, parallel, open-label study was conducted. A 2-day inpatient period was provided to establish optimal basal rate. A 5-7 day run-in period (maintained optimized basal rate; insulin requirements, episodes of hypoglycemia or hyperglycemia, dietary intake and physical activity recorded) was provided. A 3-day inpatient dosing period was performed. Carbohydrate intake was individualized (40% of total calories, equally divided among 4 meals during each study day). Basal insulin (CSII) was unchanged throughout the 3-day dosing period.

Initial Doses: HIM2 0.25 mg/kg (7.2 U/kg; 1 mg of insulin=28.7 units of insulin), p.o., in a formulation shown in Table 1, 10 minutes prior to meal, HIM2 0.125 mg/kg (3.6 U/kg; 1 mg of insulin=28.7 units of insulin), p.o., in a formulation shown in Table 1, 120 minutes post meal, and Insulin lispro (commercially available from Eli Lilly & Co., Indianapolis, Ind.) (hereinafter "Lispro"), 0.1 U/kg (0.003 mg/kg;

1 mg of insulin=28.7 units of insulin), s.c., 15 minutes prior to meal. Doses were adjusted as necessary with the next scheduled dose according to the dose titration rules described in Table 2; however, no dose titration was allowed during study day 3.

TABLE 1

| Component | Conc. | unit | % (w/v) |
|---|---|---|---|
| HIM2 | 2.5 | mg/ML | 0.25 |
| sodium cholate | 3 | % | 3.00 |
| oleic acid | 1 | % | 2.00 |
| capric acid | 0.5 | % | 0.5 |
| lauric acid | 0.5 | % | 0.5 |
| citric acid | 350 | mM | 6.72 |
| tris(hydroxymethy)aminomethane | 350 | mM | 4.24 |
| triethanolamine | 350 | mM | 5.22 |
| sucralose | 0.2 | % | 0.20 |
| strawberry flavor | 0.4 | % | 0.4 |
| sodium hydroxide | pH adjust to 7.8 | — | — |
| water | q.s. | — | — |

TABLE 2

| 240 Minute Postprandial Blood Glucose Value | HIM2 | Lispro |
|---|---|---|
| <100 mg/dL | decrease dose 20% | decrease dose 20% |
| 100-200 mg/dL | maintain same dose | maintain same dose |
| >200 mg/dL | increase dose 50% | increase dose 20% |

Assays: Plasma glucose: glucose oxidase-based enzymatic assay. Plasma insulin: RIA method (Linco Research, St. Charles, Mo.).

Efficacy Variables: The following variables were evaluated to determine efficacy of HIM2 compared to Lispro. (1) Percentage of patients able to maintain 2-hour postprandial blood glucose levels consistent with pre-study values between 80-250 mg/dL on Day 3 (HIM2 compared to insulin lispro). (2) Daily mean plasma glucose on Day 3. (3) Postprandial glucose at 2 hours during Day 3. (4) Number of rescue interventions (hypoglycemia).

Safety Variables: Adverse events, vital signs, clinical chemistry, hematology, urinalysis, and ECG monitoring.

Data Analysis: A comparison of proportion of patients within target glucose range (80-250 mg/dL) was analyzed. The daily mean plasma glucose AUC was analyzed using a t-test. The Day 3-2 hour post-prandial glucose was analyzed using a t-test. Comparison of rates for hypoglycemic events was analyzed using glucose 50-60 mg/dL, glucose $\leq$50 mg/mL, and number of rescue interventions.

Demographics: A total of 31 patients were enrolled and analyzed in this study (15 M/16 F). The majority of baseline demographic characteristics (mean±SD) for age, $HbA_{1c}$, and BMI were comparable between treatment groups: Age 39.4±9.6 vs. 39.4±9.4; $HbA_{1c}$ 7.2±0.9 vs. 7.3±0.8; and BMI 25.5±2.4 vs. 25.4±3.5 for HIM2 and insulin lispro, respectively. The average daily insulin requirement was higher in the insulin lispro group (the "control group") (n=12) 46.3±24.0 compared to 31.0±14.4 units in the HIM2 treatment group (n=19).

Safety: Safety results are provided in FIG. 1. Overall assessment of the number of hypoglycemic events demonstrated a trend toward fewer events in the HIM2 treatment group. Hypoglycemic events that required rescue intervention were significantly lower in the HIM2 treatment group as compared to the insulin lispro treatment group (control group) (p=0.04). One documented serious adverse event for hypoglycemia occurred in the HIM2 treatment group. Number and frequency of gastrointestinal side effects (i.e., primarily unpleasant taste and diarrhea) occurred more frequently in the HIM2 treatment group.

Figure 2:
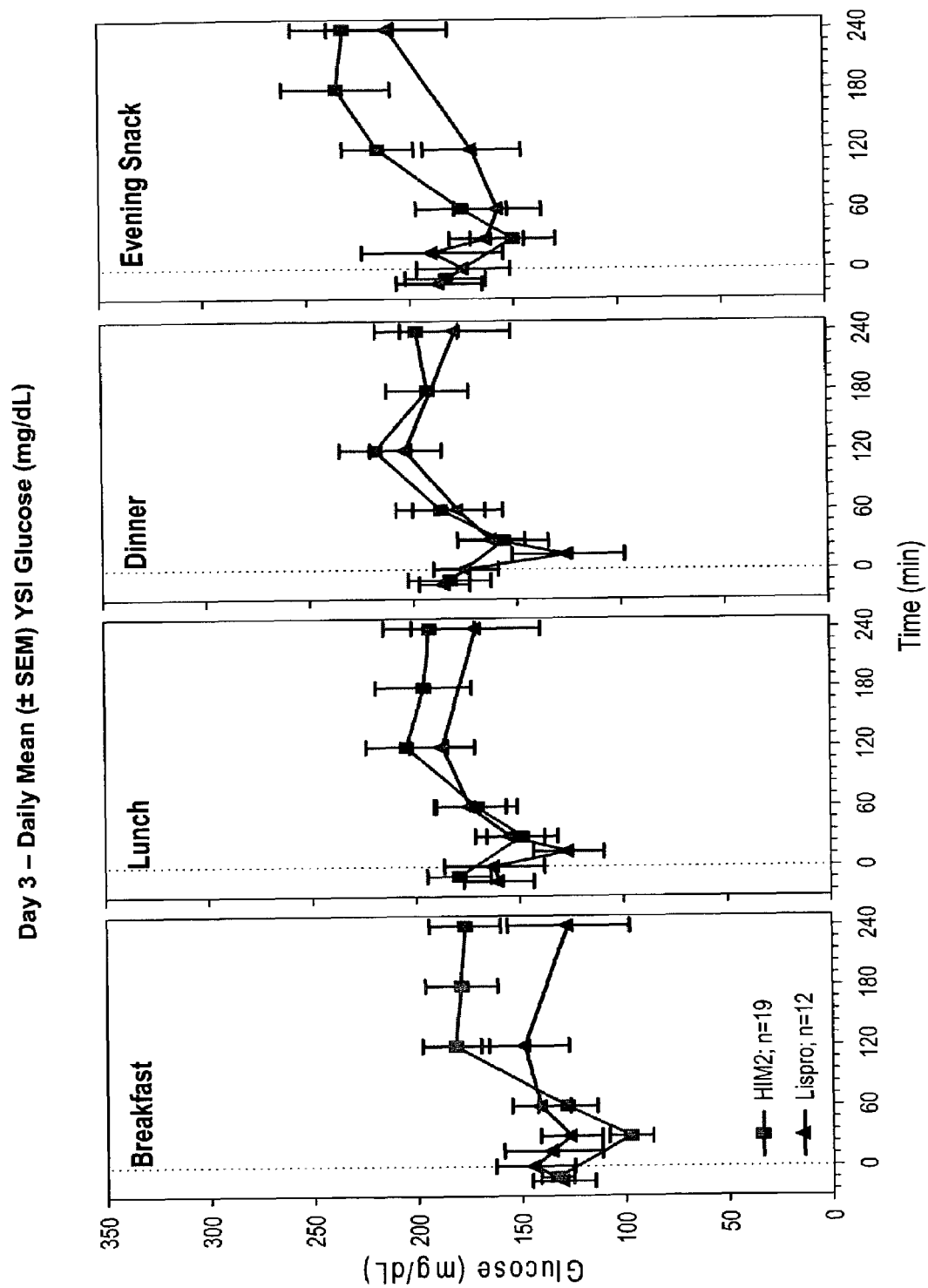
FIG. 2 shows a comparison between the daily mean (±SEM) YSI glucose levels achieved using methods according to embodiments of the present invention and the daily mean (±SEM) YSI glucose levels achieved using conventional injectable insulin (Lispro) therapy.

Glucodynamics: Glucodynamic results are provided in Tables 3 and 4 and in FIG. 2. A comparison between the treatment groups showed that 12/19 (63%) HIM2 and 10/12 (83%) insulin lispro patients (control group) had average 2-hour post-prandial glucose levels consistent with pre-study values (range 80-250 mg/dL); Fisher's exact test (p=0.42). Day 3 two-hour postprandial blood glucose values following each meal were similar between the 2 treatment groups. The mean plasma glucose AUC values (mean±SEM were similar between the two treatment groups.

TABLE 3

Day 3 - 2 Hour Post-prandial Glucose at Different Time Points (Mean ± SEM)

| Drug | Breakfast* | Lunch** | Dinner[†] | Evening Snack[‡] |
|---|---|---|---|---|
| HIM2 (n = 16) | 192.3 ± 19.4 | 232.9 ± 21.0 | 249.0 ± 19.3 | 231.4 ± 18.4 |
| Lispro (n = 12) | 158.2 ± 24.3 | 202.6 ± 16.1 | 195.3 ± 20.6 | 197.9 ± 20.4 |

*p = 0.28;
**p = 0.29;
[†]p = 0.07;
[‡]p = 0.24

TABLE 4

Day 3 - Daily Mean (±SEM) Plasma Glucose AUC (mg/dL)*

| Drug | AUC Value (mg/dL) |
|---|---|
| HIM2 (n = 16) | 182.0 ± 10.0 |
| Lispro (n = 12) | 170.6 ± 11.8 |

*p = 0.46; total 24-hour AUC in mg-min/dL is divided by 1440 to remove time from the units. The final value is time-adjusted AUC in mg/dL.

In the specification, there has been disclosed typical preferred embodiments of the invention and, although specific terms are employed, they are used in a generic and descriptive sense only and not for purposes of limitation, the scope of the invention being set forth in the following claims.

What is claimed is:

1. A method for reducing hypoglycemic episodes experienced by a human subject in need of treatment for diabetes mellitus and having a tendency toward hypoglycemic episodes, said method comprising:
orally administering an amount of an insulin polypeptide-oligomer conjugate to the human subject, wherein the insulin polypeptide-oligomer conjugate comprises an insulin polypeptide and an oligomer, wherein the oligomer comprises a hydrophilic moiety and a lipophilic moiety, wherein the insulin polypeptide-oligomer conjugate is a mono-conjugate, wherein the oligomer is coupled to an amino functionality of insulin at $Lys^{B-29}$, and wherein the amount of the insulin polypeptide-oligomer conjugate orally administered to the subject maintains the subject's blood glucose level between 80 mg/dl and 250 mg/dl and reduces the number and/or severity of hypoglycemic episodes experienced by the human subject during a given time period when compared with the number and/or severity of hypoglycemic episodes that would have been experienced during a similar time period by the human subject parenterally administered insulin or an insulin analog in an amount that provides a substantially equivalent level of glycemic control.

2. The method of claim 1, wherein the amount of the insulin polypeptide oligomer conjugate orally administered to the subject is between 0.05 and 5 mg per kilogram body weight.

3. The method of claim 1, wherein the amount of insulin polypeptide-oligomer conjugate orally administered to the subject reduces the number of hypoglycemic episodes experienced by the subject.

4. The method of claim 1, wherein the amount of insulin polypeptide-oligomer conjugate orally administered to the subject reduces the severity of hypoglycemic episodes experienced by the subject.

5. The method of claim 1, wherein the insulin polypeptide of the insulin polypeptide-oligomer conjugate comprises:
    a lysine at B-29;
    an A chain having an N terminus;
    a B chain having an N terminus; and
    wherein the oligomer of the insulin polypeptide-oligomer conjugate is coupled to the lysine at B-29.

6. The method of claim 1, wherein the hydrophilic moiety is a polyalkylene glycol moiety.

7. The method of claim 1, wherein the lipophilic moiety is an alkyl or fatty acid moiety.

8. The method of claim 1, wherein the insulin polypeptide-oligomer conjugate comprises the structure of Formula V:

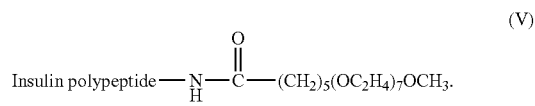

9. The method of claim 1, wherein the amount of the insulin polypeptide-oligomer conjugate orally administered to the subject maintains the subject's blood glucose level between 70 mg/dl and 120 mg/dl when measured before a meal.

10. The method of claim 1, wherein the amount of the insulin polypeptide-oligomer conjugate orally administered to the subject maintains the subject's blood glucose level at less than 180 mg/dl but more than 70 mg/dl when measured within two hours after a meal.

* * * * *

UNITED STATES PATENT AND TRADEMARK OFFICE
CERTIFICATE OF CORRECTION

PATENT NO. : 7,601,688 B2
APPLICATION NO. : 10/461199
DATED : October 13, 2009
INVENTOR(S) : Still et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 783 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,688 B2 | Page 1 of 1 |
| APPLICATION NO. | : 10/461199 | |
| DATED | : October 13, 2009 | |
| INVENTOR(S) | : James Gordon Still et al. | |

It is certified that error appears in the above-identified patent and that said Letters Patent is hereby corrected as shown below:

Column 1, line 14: add "...on February 15, 2001; and claims priority to U.S. Provisional Application No. 60/388,988 filed on June 13, 2002."

Signed and Sealed this

Eighth Day of March, 2011

David J. Kappos
*Director of the United States Patent and Trademark Office*